US008529426B2

(12) United States Patent
Boyden et al.

(10) Patent No.: US 8,529,426 B2
(45) Date of Patent: Sep. 10, 2013

(54) IONIZING-RADIATION-RESPONSIVE COMPOSITIONS, METHODS, AND SYSTEMS

(75) Inventors: Edward S. Boyden, Cambridge, MA (US); Roderick A. Hyde, Redmond, WA (US); Muriel Y. Ishikawa, Livermore, CA (US); Edward K. Y. Jung, Bellevue, WA (US); Nathan P. Myhrvold, Medina, WA (US); Clarence T. Tegreene, Bellevue, WA (US); Thomas A. Weaver, San Mateo, CA (US); Charles Whitmer, North Bend, WA (US); Lowell L. Wood, Jr., Bellevue, WA (US); Victoria Y. H. Wood, Livermore, CA (US)

(73) Assignee: The Invention Science Fund I LLC

( * ) Notice: Subject to any disclaimer, the term of this patent is extended or adjusted under 35 U.S.C. 154(b) by 1473 days.

(21) Appl. No.: 12/012,220

(22) Filed: Jan. 30, 2008

(65) Prior Publication Data

US 2009/0101840 A1    Apr. 23, 2009

Related U.S. Application Data

(63) Continuation-in-part of application No. 11/975,702, filed on Oct. 18, 2007, now Pat. No. 8,164,074.

(51) Int. Cl.
*A61N 5/00* (2006.01)
(52) U.S. Cl.
USPC ........................................... 600/3; 250/472.1
(58) Field of Classification Search
USPC ............................ 600/1–8; 250/472.1–488.1
See application file for complete search history.

(56) References Cited

U.S. PATENT DOCUMENTS

| 5,378,897 | A  | 1/1995  | Suzuki |
| 5,470,307 | A  | 11/1995 | Lindall |
| 5,482,719 | A  | 1/1996  | Guillet et al. |
| 5,773,592 | A  | 6/1998  | Mills |
| 5,807,534 | A  | 9/1998  | Pomato et al. |
| 5,829,448 | A  | 11/1998 | Fisher et al. |
| 5,997,842 | A  | 12/1999 | Chen |
| 5,998,580 | A  | 12/1999 | Fay et al. |
| 6,040,194 | A  | 3/2000  | Chick et al. |
| 6,207,392 | B1 | 3/2001  | Weiss et al. |
| 6,344,050 | B1 | 2/2002  | Chen |
| 6,397,102 | B1 | 5/2002  | Neuberger |
| 6,433,931 | B1 | 8/2002  | Fink et al. |
| 6,451,346 | B1 | 9/2002  | Shah et al. |
| 6,493,570 | B1 | 12/2002 | Dees et al. |

(Continued)

FOREIGN PATENT DOCUMENTS

| WO | WO 96/23543    | 8/1996 |
| WO | WO 99/52565 A1 | 10/1999 |
| WO | WO 00/36983 A1 | 6/2000 |
| WO | WO 2005/058360 A2 | 6/2005 |

OTHER PUBLICATIONS

Davila, Jorge et al.; "Inactivation of Tumours and Viruses via Efficient Photoisomerisation"; J. Chem. Soc., Chem Commun.; 1989; pp. 1215-1216.

(Continued)

*Primary Examiner* — Charles A Marmor, II
*Assistant Examiner* — Carrie R Dorna

(57) ABSTRACT

A method, composition and system respond to ionizing radiation to adjust biological activity. In some approaches the ionizing radiation is X-ray or extreme ultraviolet radiation that produces luminescent responses that induce biologically active responses.

6 Claims, 15 Drawing Sheets

(56) References Cited

U.S. PATENT DOCUMENTS

| | | | |
|---|---|---|---|
| 6,514,481 B1 | 2/2003 | Prasad et al. |
| 6,631,283 B2 | 10/2003 | Storrie et al. |
| 6,777,237 B2 | 8/2004 | Grissom et al. |
| 7,066,904 B2 | 6/2006 | Rosenthal et al. |
| 7,067,072 B2 | 6/2006 | Chen |
| 7,364,754 B2 | 4/2008 | Prasad et al. |
| 2002/0049154 A1 | 4/2002 | Grissom et al. |
| 2002/0127224 A1 | 9/2002 | Chen |
| 2003/0191458 A1 | 10/2003 | Diamond et al. |
| 2003/0216284 A1 | 11/2003 | Fink et al. |
| 2003/0232011 A1 | 12/2003 | Griffiths et al. |
| 2004/0180096 A1 | 9/2004 | Prasad et al. |
| 2005/0260131 A1 | 11/2005 | Amaratunga et al. |
| 2006/0222587 A1 | 10/2006 | Prasad et al. |
| 2006/0258587 A1 | 11/2006 | Kocer et al. |
| 2007/0063154 A1 | 3/2007 | Chen et al. |
| 2007/0117089 A1 | 5/2007 | Croker et al. |
| 2007/0128662 A1 | 6/2007 | Isacoff et al. |
| 2007/0217996 A1 | 9/2007 | Levy et al. |
| 2007/0218049 A1 | 9/2007 | Chen et al. |
| 2008/0139993 A1 | 6/2008 | Bensaoula et al. |
| 2008/0193431 A1 | 8/2008 | Zheng et al. |

OTHER PUBLICATIONS

UK Intellectual Property Office Search Report Under Section 17; App. No. GB0818996.1; bearing a date of Feb. 11, 2009; pp. 1-2.

Atanasijevic, Tatjana et al.; "Calcium-Sensitive MRI Contrast Agents Based on Superparamagnetic Iron Oxide Nanoparticles and Calmodulin"; PNAS; Oct. 3, 2006; pp. 14707-14712; vol. 103, No. 40.

Ball, Philip; "Light Pumps Drugs From Nanoparticles"; Nanozone News; Jun. 9, 2005; pp. 1-3; located at: http://www.nature.com/materials/nanozone/news/050609/portal/m05 . . . ; printed on Apr. 27, 2007.

Banghart, Matthew et al.; "Light-Activated Ion Channels for Remote Control of Neuronal Firing"; Nature Neuroscience; Dec. 2004; pp. 1381-1386; vol. 7, No. 12; Nature Publishing Group.

Bergey, Earl; Prasad, Paras; "Small Spheres, Big Potential"; Spie's OE Magazine; Jul. 2003; pp. 26-29.

Blasse, G.; Grabmaier, B.C.: *Luminescent Materials*; 1994; 233 pages; ISBN 3-540-58019-0; Springer-Verlag (not provided).

Blasse, G.; Brixner, L.H.; "X-Ray-Excited Luminescence of Samarium (III), Europium (III), Gadolinium (III) and Terbium (III) 2.2.1 Cryptates"; Chemical Physics Letters; Jun. 23, 1989; pp. 504-508 (p. 1); vol. 158, Issue 6; located at: http://www.sciencedirect.com/science?_ob=ArticleURL&_udi=B6TF; printed on Apr. 18, 2007.

Boyer, Arthur L. et al.; "Radiation in the Treatment of Cancer"; Physics Today; Sep. 2002; pp. 1-5; American Institute of Physics; located at: http://www.physicstoday.org/vol-55/iss-9/p34.html; printed on Oct. 10, 2007.

Boyer, Arthur L.; "The Physics of Intensity-Modulated Radiation Therapy"; Physics Today; Sep. 2002; pp. 38-43; American Institute of Physics.

Chen, Wei et al.; "The Origin of X-Ray Luminescence from CdTe Nanoparticles in CdTe/BaFBr:Eu$^{2+}$ Nanocomposite Phosphors"; Journal of Applied Physics; 2006; pp. 034302-1 to 034302-5; vol. 99; American Institute of Physics.

Chen, Wei; Zhang, Jun; "Using Nanoparticles to Enable Simultaneous Radiation and Photodynamic Therapies for Cancer Treatment"; Journal of Nanoscience and Nanotechnology; 2006; pp. 1159-1166; vol. 6, No. 4; American Scientific Publishers.

Dubertret, Benoit et al.; "In Vivo Imaging of Quantum Dots Encapsulated in Phospholipid Micelles"; Science; Nov. 29, 2002; pp. 1759-1762; vol. 298.

Eisenman, Lawrence N. et al.; "Anticonvulsant and Anesthetic Effects of a Fluorescent Neurosteroid Analog Activated by Visible Light"; Nature Neuroscience; 2007; pp. 1-8; Nature Publishing Group.

Erwin, Steven C. et al.; "Doping Semiconductor Nanocrystals"; Nature; Jul. 7, 2005; pp. 91-94; vol. 436; Nature Publishing Group.

Hardman, Ron; "A Toxicologic Review of Quantum Dots: Toxicity Depends on Physicochemical and Environmental Factors"; Environmental Health Perspectives; Feb. 2006; pp. 165-172; vol. 114, No. 2.

Hermanson, Greg T.; *Bioconjugate Techniques*; 1996; 785 pages; ISBN 0123423368; Academic Press; (not provided).

Holm, Bruce A. et al.; "Nanotechnology in BioMedical Applications"; Mol. Cryst. Liq. Cryst.; 2002; pp. 589-598; vol. 374; Taylor and Francis.

Kehayova, Polina D. et al.; "Phototriggered Delivery of Hydrophobic Carbonic Anhydrase Inhibitors"; Photochem. Photobiol. Sci.; 2002; pp. 774-779; vol. 1; The Royal Society of Chemistry and Owner Societies.

Koçer, Armağan et al.; "A Light-Actuated Nanovalve Derived from a Channel Protein"; Science; Jul. 29, 2005; pp. 755-758; vol. 309.

Kumita, Janet R. et al.; "Photo-Control of Helix Content in a Short Peptide"; PNAS; Apr. 11, 2000; pp. 3803-3808; vol. 97, No. 8.

Letant, S.E.; Wang, T.F.; "Semiconductor Quantum Dot Scintillation Under Gamma-Ray Irradiation"; Nano Letters; Aug. 30, 2006; 14 Total Pages.

Letant, S.E.; Wang, T.F.; "Study of Porous Glass Doped with Quantum Dots or Laser Dyes Under Alpha Irradiation"; Applied Physics Letters; 2006; pp. 103110-1 to 103110-3; vol. 88; American Institute of Physics.

Levy, Laurent et al.; "Nanochemistry: Synthesis and Characterization of Multifunctional Nanoclinics for Biological Applications"; Chem. Mater.; 2002; pp. 3715-3721; vol. 14; American Chemical Society.

Li, Wen-Hong; "Crafting New Cages"; Nature Methods; Jan. 2006; pp. 13-15; vol. 3, No. 1; Nature Publishing Group.

Mamada, Akira et al.; "Photoinduced Phase Transition of Gels"; Macromolecules; 1990; pp. 1517-1519 (p. 1); vol. 23; American Chemical Society.

Michalet, X. et al.; "Quantum Dots for Live Cells, in Vivo Imaging, and Diagnostics"; Science; Jan. 28, 2005; pp. 538-544 (pp. 1-16); vol. 307.

Momotake, Atsuya et al.; "The Nitrodibenzofuran Chromophore: A New Caging Group for Ultra-Efficient Photolysis in Living Cells"; Nature Methods; Jan. 2006; pp. 35-40; vol. 3, No. 1; Nature Publishing Group.

Monson, Eric et al.; "PEBBLE Nanosensors for in vitro bioanalysis"; Biomedical Photonics Handbook; 2003; 9 Total Pages; Chapter 59; CRC Press.

"Nanotechnology Tackles Brain Cancer"; NCI Alliance for Nanotechnology in Cancer; Dec. 2005; pp. 1-4.

Nikl, Martin; "Scintillation Detectors for X-Rays"; Measurement Science and Technology; 2006; pp. R37-R54; vol. 17; Institute of Physics Publishing.

"Polymers That Shrink From Light"; Science News; Sep. 1, 1990; p. 1; located at: http://findarticles.com/p/articles/mi_m1200/is_n9_v138/ai_9397237/print; printed on Jun. 22, 2007.

Prasad, Paras N.; *Introduction to Biophotonics*; Apr. 2003; 616 pages; ISBN 0471287709; Wiley-Interscience; (not provided).

Roby, Aruna et al.; "Solubilization of Poorly Soluble PDT Agent, Mesotetraphenylporphin, in Plain or Immunotargeted PEG-PE Micelles Results in Dramatically Improved Cancer Cell Killing in Vitro"; Eur. J. Pharm. Biopharm.; Apr. 2006; pp. 235-240 (pp. 1-12); vol. 62, No. 3.

Rosenberg, R.A. et al.; "X-Ray Excited Optical Luminescence Studies of ZnS and ZnO Nanostructures"; SRMS-5 Conference; Jul. 30-Aug. 2, 2006; p. 1.

Shi, Lixin et al.; "Singlet Oxygen Generation from Water-Soluble Quantum Dot-Organic Dye Nanocomposites"; J. Am. Chem. Soc.; 2006; pp. 6278-6279; vol. 128; American Chemical Society.

Sitharaman, B. et al.; "Superparamagnetic Gadonanotubes are High-Performance MRI Contrast Agents"; Chem. Commun.; 2005; pp. 3915-3917; The Royal Society of Chemistry.

Soo, Y.L. et al.; "X-Ray Excited Luminescence and Local Structures in Tb-Doped $Y_2O_3$ Nanocrystals"; Journal of Applied Physics; May 15, 1998; pp. 5404-5409; vol. 83, No. 10; American Institute of Physics.

Speert, Debra; "Neurotechniques"; Neuroscience Gateway; Mar. 2007; 2 Total Pages; located at: http://www.brainatlas.org/aba/2007/070315/full/aba1726.shtr; printed on Jun. 12, 2007.

Suzuki, Atsushi; Tanaka, Toyoichi; "Phase Transition in Polymer Gels Induced by Visible Light"; Nature; Jul. 26, 1990; pp. 345-347 (pp. 1-2); vol. 346; located at: http://www.nature.com/nature/journal/v346/n6282/abs/346345a0.html; printed on Oct. 10, 2007.

Unger, S.A.; "Photodynamic Therapy: A Bench-to-Bedside Success Story"; Buffalo Physician; Autumn 2004; pp. 8-19.

Van Eijk, Carel W.E.; "Inorganic Scintillators in Medical Imaging"; Physics in Medicine and Biology; 2002; pp. R85-R106; vol. 47; Institute of Physics Publishing.

Vo-Dinh, Tuan; *Biomedical Photonics Handbook*; Mar. 26, 2003; 1872 pages; ISBN 0849311160; CRC; (not provided).

Volgraf, Matthew et al.; "Allosteric Control of an Ionotropic Glutamate Receptor with an Optical Switch"; Nat. Chem. Biol.; Jan. 2006; pp. 47-52 (pp. 1-13); vol. 2, No. 1.

Von Seggern, Heinz; "Photostimulable X-Ray Storage Phosphors: A Review of Present Understanding"; Brazilian Journal of Physics; Jun. 1999; pp. 254-268; vol. 29, No. 2.

Wang, Shizhong et al.; "Nanomaterials and Singlet Oxygen Photosensitizers: Potential Applications in Photodynamic Therapy"; Journal of Materials Chemistry; 2004; pp. 487-493; vol. 14; The Royal Society of Chemistry.

"Watery Nanoparticles Deliver Anticancer Therapy"; NCI Alliance for Nanotechnology in Cancer; Mar. 5, 2007; p. 1; located at: http://nano.cancer.gov/news_center/2007/march/nanotech_news_200; printed on Mar. 13, 2007.

Wieder, Martina E. et al.; "Intracellular Photodynamic Therapy with Photosensitizer—Nanoparticle Conjugates: Cancer Therapy Using a 'Trojan Horse'"; Photochemical and Photobiological Sciences; 2006; pp. 727-734; vol. 5; The Royal Society of Chemistry and Owner Societies.

Yao, W.M. et al.; "'27. Passage of Particles Through Matter' and '28. Particle Detectors'"; *Review of Particle Physics*; Journal of Physics G: Nuclear and Particle Physics; 2006; pp. 258-292; vol. 33, No. 1; located at: http://www.iop.org/EJ/article/0954-3899/33/1/001/g_33_1_001.html.

Zhang, Tingting et al.; "Cellular Effect of High Doses of Silica-Coated Quantum Dot Profiled with High Throughput Gene Expression Analysis and High Content Cellomics Measurements"; Nano Letters; 2006; pp. 800-808; vol. 6, No. 4; American Chemical Society.

Luzgina et al.; "Hematoporphyrin IX Physicochemical Properties, Synthesis, Biological Activity, and Clinical Use"; Pharmaceutical Chemistry Journal; May 1977; pp. 613-620; vol. 11, No. 5; Plenum Publishing Corporation, New York; printed by examiner on Jul. 25, 2012.

U.S. Appl. No. 12/012,229, filed Jan. 30, 2008, Boyden et al.
U.S. Appl. No. 12/012,209, filed Jan. 30, 2008, Boyden et al.
U.S. Appl. No. 12/012,217, filed Jan. 30, 2008, Boyden et al.
U.S. Appl. No. 12/012,233, filed Jan. 30, 2008, Boyden et al.
U.S. Appl. No. 12/012,218, filed Jan. 30, 2008, Boyden et al.

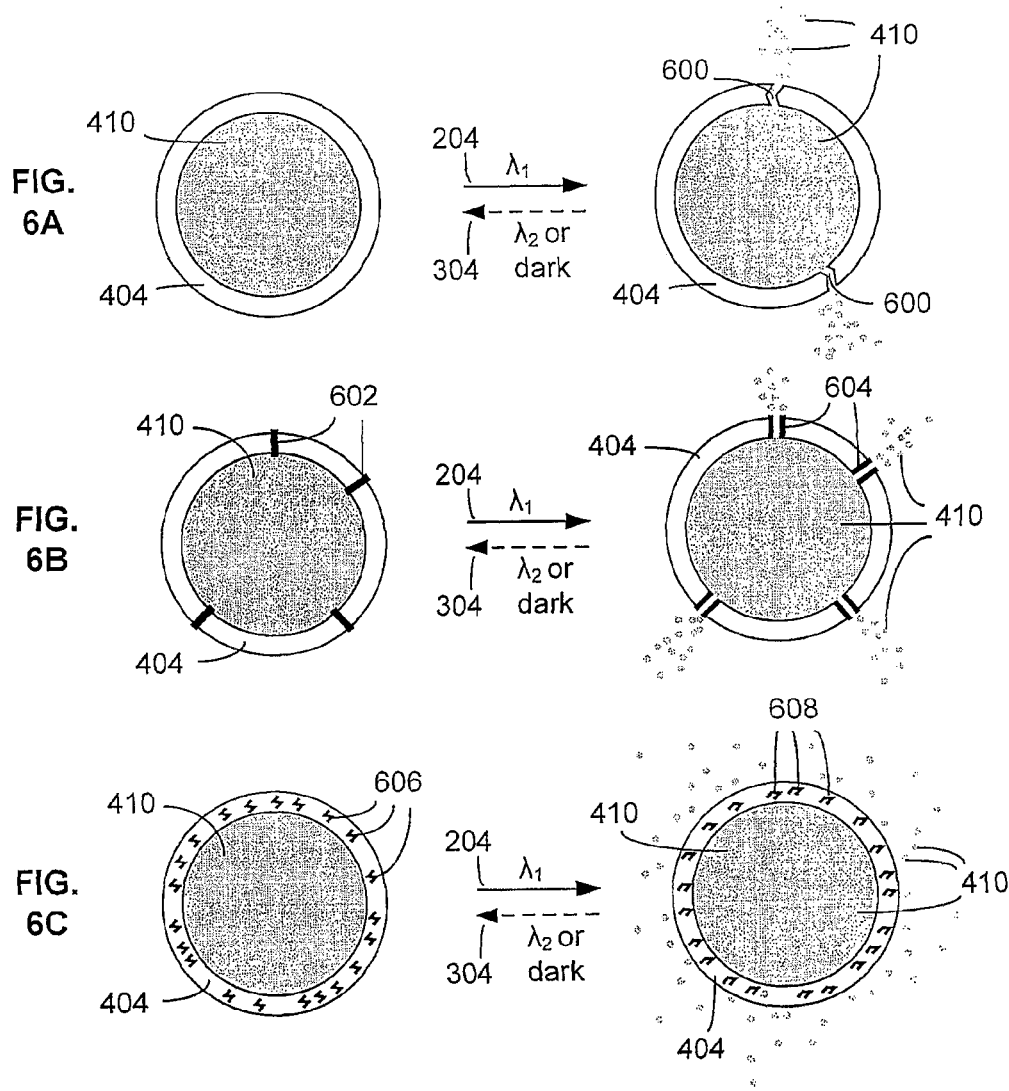

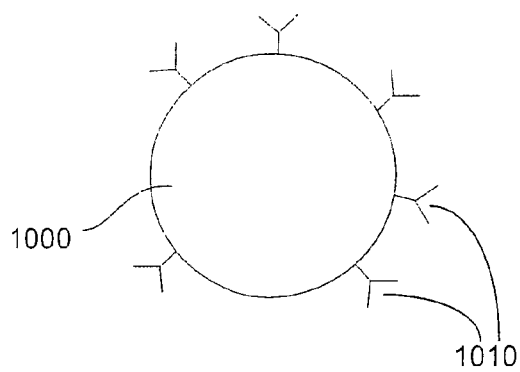
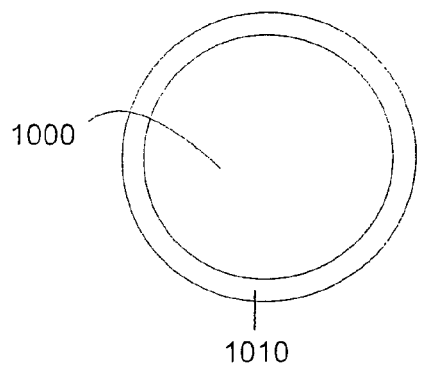
FIG. 10A            FIG. 10B
FIG. 12
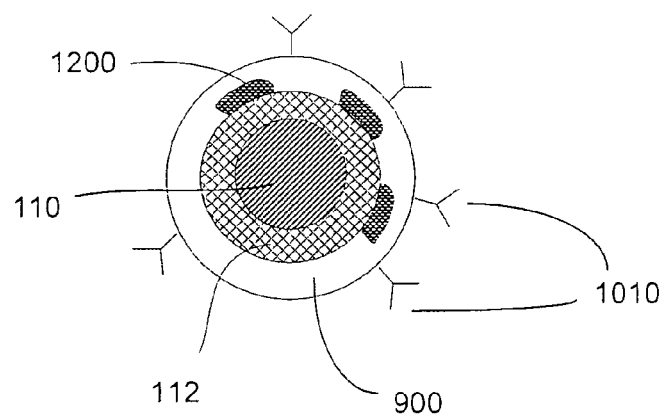

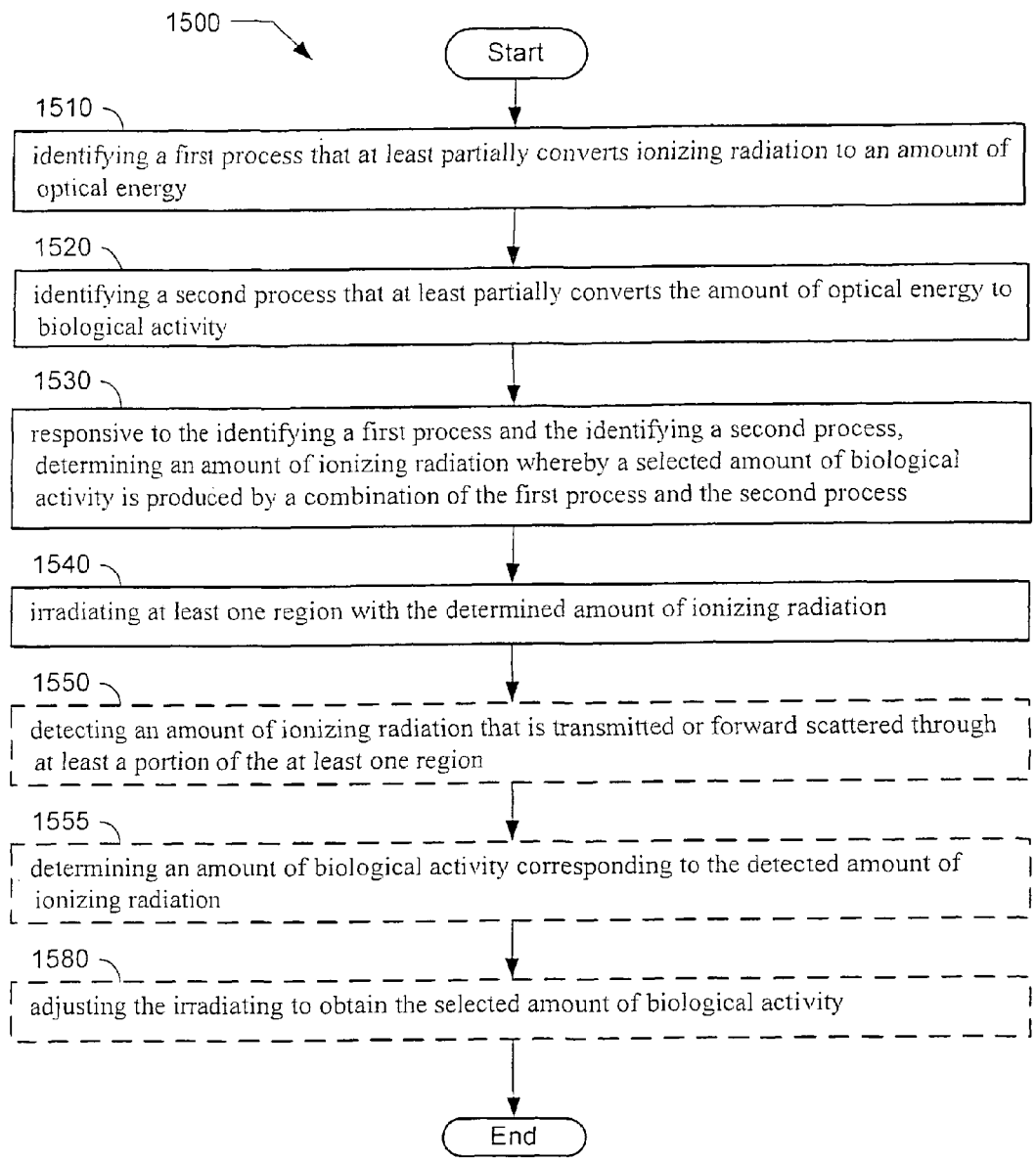

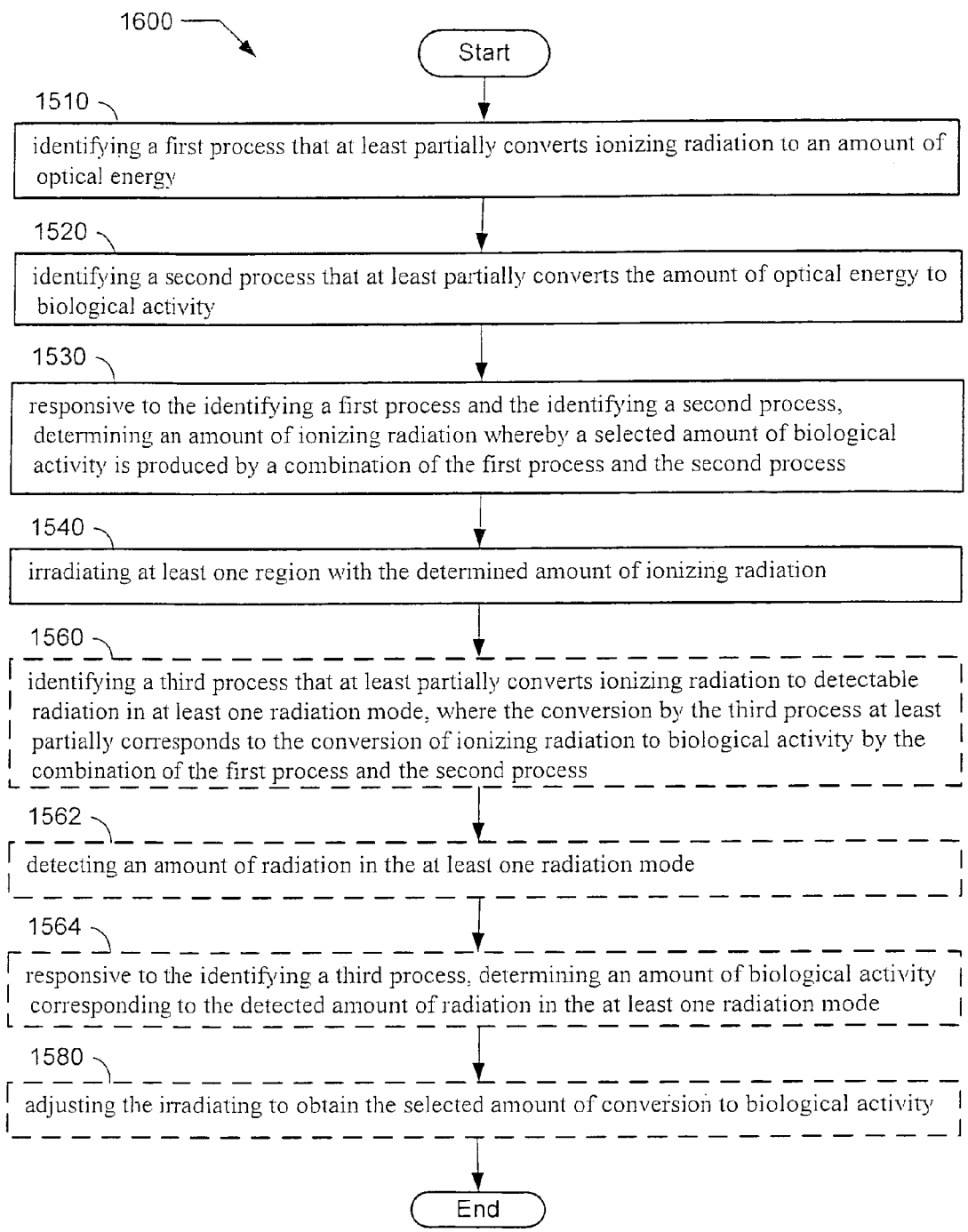

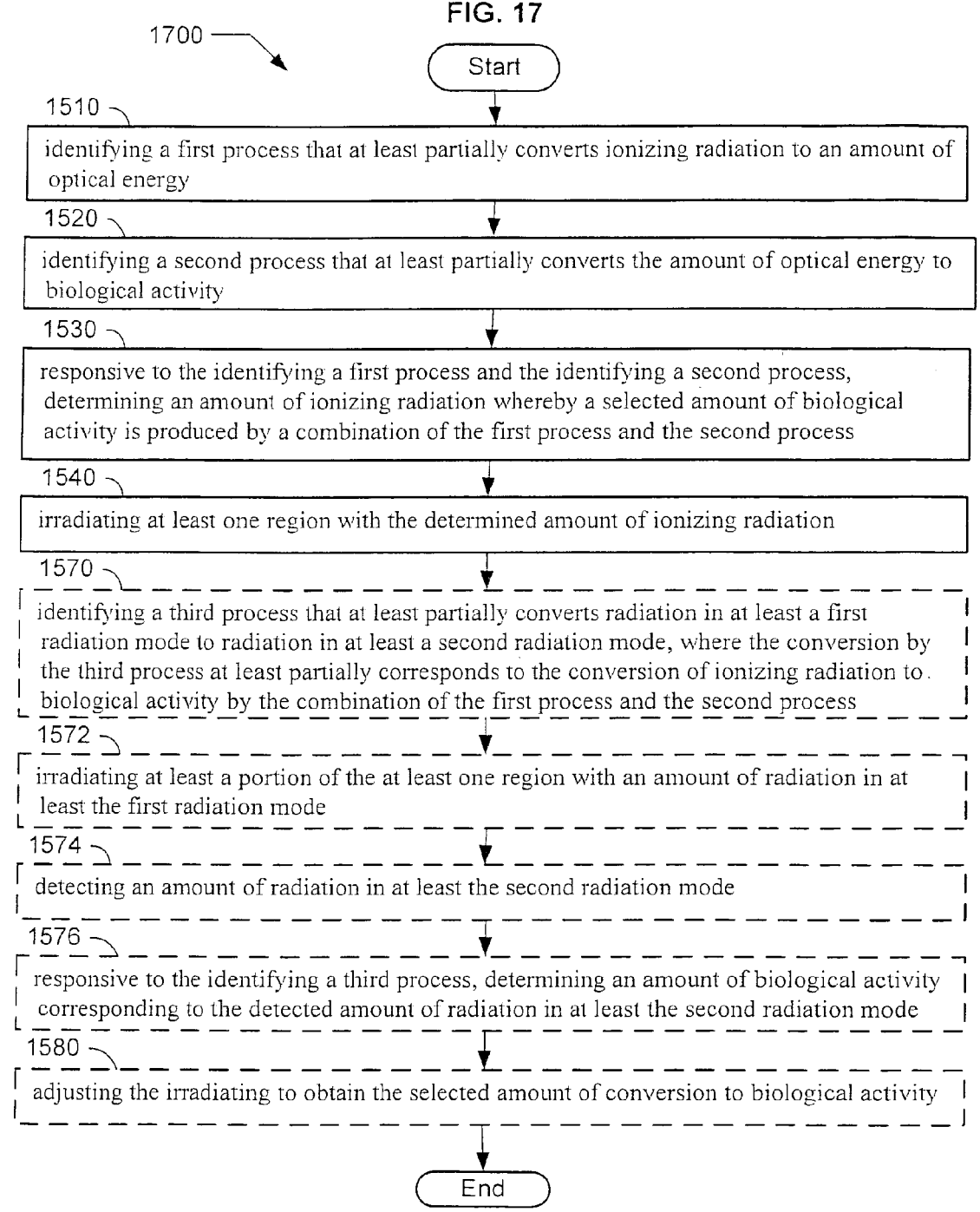

IONIZING-RADIATION-RESPONSIVE COMPOSITIONS, METHODS, AND SYSTEMS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/975,702, entitled IONIZING-RADIATION-RESPONSIVE COMPOSITIONS, METHODS, AND SYSTEMS, naming Edward S. Boyden; Roderick A. Hyde; Muriel Y. Ishikawa; Edward K. Y. Jung; Nathan P. Myhrvold; Clarence T. Tegreene; Thomas A. Weaver; Charles Whitmer; Lowell L. Wood, Jr. and Victoria Y. H. Wood as inventors, filed 18 Oct. 2007 now U.S. Pat. No. 8,164,074.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BRIEF DESCRIPTION OF THE FIGURES

FIGS. 5A-5C and 6A-6C depict configurations of a photosensitive bioactivity-adjusting material and a biologically active material.

FIGS. 8A-8G, 9A-9H, 10A-10B, 11A-11D, and 12 depict ionizing-radiation-responsive compositions.

FIGS. 15-17 depict process flows.

DETAILED DESCRIPTION

Figure 1:
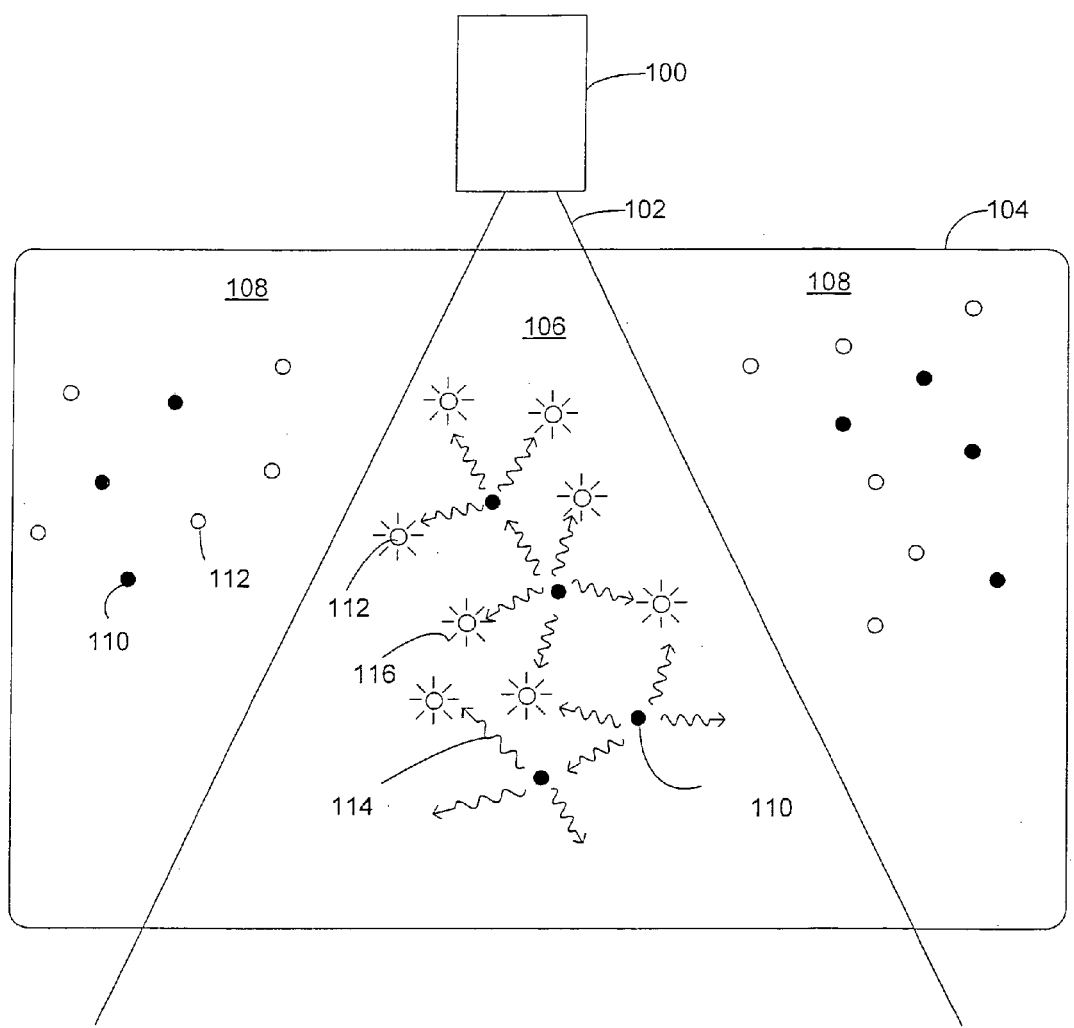
FIG. 1 depicts irradiation of an ionizing-radiation-responsive composition.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 depicts an illustrative embodiment in which an ionizing radiation emitter 100 produces ionizing radiation 102. The ionizing radiation irradiates at least a portion of a region 104 that contains a luminescent material 110 and a photosensitive biologically active material 112. The region 104 might include, for example, a human or animal patient or a portion thereof, such as the head, neck, limb, thorax, spine, abdomen, or pelvis; or a particular tissue, organ, or gland; or a particular lesion caused by disease or injury; or any other area selected for treatment. In the illustrative embodiment depicted in FIG. 1, the beam of ionizing radiation partitions the region 104 into an irradiated region 106 and a non-irradiated region 108. In the irradiated region 106, the luminescent material responds to ionizing radiation 102 to produce optical energy 114, and the photosensitive biologically active material responds to the optical energy 114 to become biologically active, as indicated schematically in FIG. 1 by the radial lines 116 (other embodiments provide other responses of the photosensitive biologically active material; for example, the photosensitive biologically active material may respond to the optical energy 114 to become biologically inactive, to partially increase or decrease a level of biological activity, to change from a first mode of biological activity to second mode of biological activity, etc.). In the non-irradiated region 108, the luminescent material does not receive ionizing radiation, so it does not produce optical energy to activate the photosensitive biologically active material.

In general, the term "photosensitive biologically active material" can encompass any material having a biological activity that changes in response to optical energy. For example, the photosensitive biologically active material can include a material that is biologically inactive and responds to optical energy to become biologically active, a material that is biologically active and responds to optical energy to become biologically inactive, a material that has a first level of biological activity and responds to optical energy to change to a second level of biological activity, a material that has a first mode of biological activity and responds to optical energy to change to a second mode of biological activity, or any other material or combination of materials having any response to optical energy that may affect its biological activity.

In some embodiments, the photosensitive biologically active material is a photosensitizer that responds to optical light by generating a reactive oxygen species (such as singlet oxygen) or another cytotoxic agent. Photosensitizers are sometimes used to destroy cancerous or diseased cells by a procedure known as photodynamic therapy (PDT). Generally this procedure involves: (1) administration of a photosensitizing drug; (2) selective uptake or retention of the photosensitizing drug in the target tissue or lesion; (3) delivery of optical light to the target tissue or lesion; (4) light absorption by the photosensitizing drug to generate a cytotoxic agent that damages or destroys the target tissue or lesion; and (5) metabolism or excretion of the photosensitizing drug to reduce sunlight sensitivity. Photodynamic therapy and photosensitizers and their uses are further described in S. A. Unger, "Photodynamic Therapy," Buffalo Physician, Autumn 2004, 8-19; Paras N. Prasad, *Introduction to Biophotonics*, Wiley-Interscience, 2003, 433-463; and Tuan Vo-Dinh et al, *Biomedical Photonics Handbook*, CRC Press, 2003, 36-1 to 38-16; which are herein incorporated by reference. Some examples of photosensitizers include porphyrins, chlorins, bacteriochlorins, benzoporphyrins, flavins, texaphyrins, phthalocyanines, naphthalocyanines, cationic dyes, halogenated xanthenes, dendrimers, fullerenes, organometallic complexes, and semiconductor nanoparticles; also, combinations or derivatives of these various compounds, and pharmaceutical preparations thereof. Some applications involve the administration of a photosensitizer metabolic precursor; an example is 5-aminolaevulinic acid (ALA), which endogenously generates the photosensitizer photoporphyrin IX.

Figure 2:
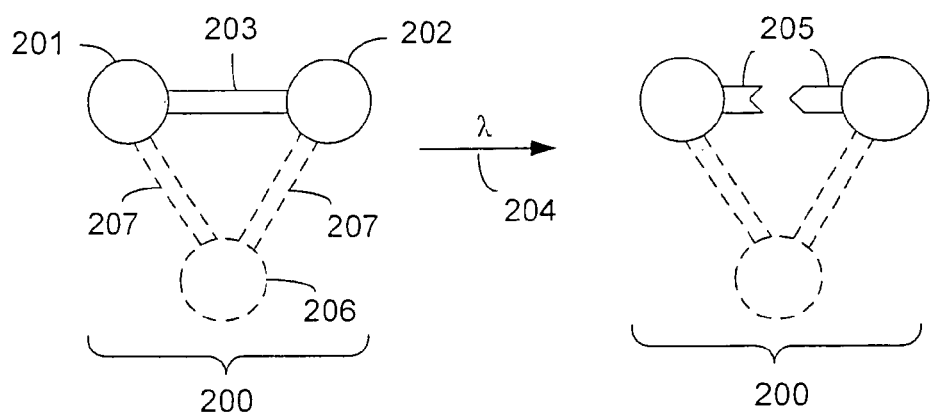
FIG. 2 depicts a photolabile material.

In some embodiments, the photosensitive biologically active material can include a photolabile material. FIG. 2 is a schematic depiction of a photolabile material 200, having a first component 201 and a second component 202 joined by a photolabile component 203. Those elements depicted with dashed lines are optional in some embodiments. The material is responsive to optical energy in at least one wavelength band, as depicted by the arrow 204 labeled with a wavelength $\lambda$, to divide the photolabile component into two fragments 205. Those of skill in the art use various terms to describe this response to optical energy, including for example "photolysis," "photodissociation," "photo-release," and "photo-uncaging." If the photolabile component 203 is the only structure that couples the first component and the second component, then the material may be completely cleaved in response to optical energy in the at least one wavelength band. If the material 200 optionally includes a third component 206 joined to the first component 201 and the second component 202 by non-photolabile components 207, then the structure is modified in response to optical energy in the at least one wavelength band, but the material is not completely cleaved and the first and second components remain indirectly coupled. The modified or cleaved structure can have a biological activity that differs from that of the unmodified or uncleaved structure.

Various photosensitive biologically active materials that include photolabile materials are known to those skilled in the art. Some representative examples are as follows; other embodiments will be apparent to those skilled in the art. Fay et al, "Photosensitive caged macromolecules," U.S. Pat. No. 5,998,580, herein incorporated by reference, describes various peptides incorporating a photolabile molecule (e.g. 2-nitrophenyl, 2-nitrobenzyloxycarbonyl, or $\alpha$-carboxy 2-nitrobenzyl) and responsive to optical energy to become biologically active or inactive. Grissom et al, "Bioconjugates and delivery of bioactive agents," U.S. Pat. No. 6,777,237, herein incorporated by reference, describes an example of a bioactive agent bonded to a cobalt atom in an organocobalt complex, where the complex responds to light to cleave the bond between the bioactive agent and the cobalt atom, thereby releasing the bioactive agent. Kehayova et al, "Photoriggered delivery of hydrophobic carbonic anhydrase inhibitors," Photochem. Photobiol. Sci. 1 (2002), 774-779, herein incorporated by reference, describes a carbonic anhydrase inhibitor bearing a photolabile cage compound, o-nitrodimethoxyphenylglycine (o-NDMPG) and responsive to optical light to photo-uncage (and thereby activate) the inhibitor molecule. W. Neuberger, "Device and method for photoactivated drug therapy," U.S. Pat. No. 6,397,102, herein incorporated by reference, describes a drug that is encapsulated in or attached to a photolabile fullerene molecule; when the inactive drug-fullerene complex is subjected to selective irradiation, the complex is broken and the drug is released in an active form. A. Momotake et al, "The nitrodibenzofuran chromophore: a new caging group for ultra-efficient photolysis in living cells," Nature Methods 30 (2006), 35-40, and W. H. Li, "Crafting new cages," Nature Methods 30 (2006), 13-15, both herein incorporated by reference, describe a photolabile nitrodibenzofuran caging group. V. Tassel et al, "Photolytic drug delivery systems," International Application No. PCT/US96/01333, and A. W. Lindall, "Catheter system for controllably releasing a therapeutic agent at a remote tissue site," U.S. Pat. No. 5,470,307, both herein incorporated by reference, describe a therapeutic or diagnostic agent bound to a polymer, metal, glass, silica, quartz, or other substrate by a photolabile linking agent (e.g. a 2-nitrophenyl, acridine, nitroaromatic, arylsulfonamide, or similar chromophore), responsive to optical light to release the therapeutic or diagnostic agent from the substrate. Guillet et al, "Drug delivery systems," U.S. Pat. No. 5,482,719, herein incorporated by reference, describes in one embodiment a polymer and a therapeutic compound, chemically bonded together through a photolabile covalent chemical linkage (e.g. a photolabile peptide blocker compound), and responsive to light to release the therapeutic compound from the polymer combination.

Figure 3:
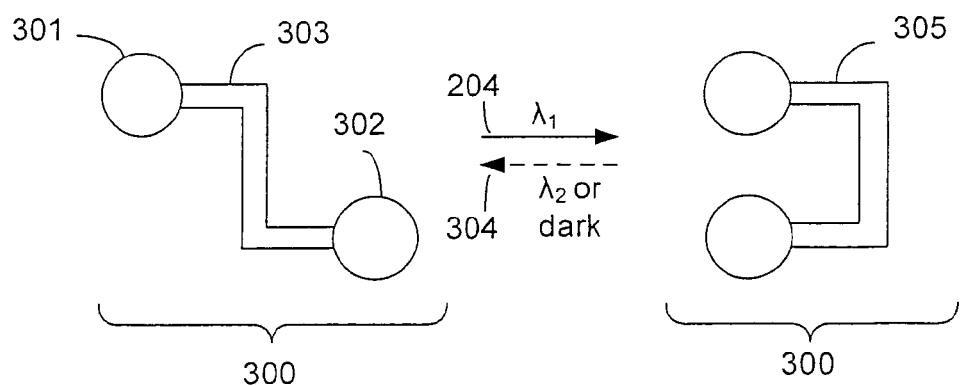
FIG. 3 depicts a photoisomerizable material.

In some embodiments, the photosensitive biologically active material can include a photoisomerizable material. FIG. 3 is a schematic depiction of a photoisomerizable material 300, having a first component 301 and a second component 302 joined by a photoisomer component in a first isomeric form 303. The material is responsive to optical energy in at least a first wavelength band, as depicted by the arrow 204 labeled with a wavelength $\lambda_1$, to convert the photoisomer component to a second isomeric form 305. The shape change depicted in the figure is a schematic representation of isomerization and is not intended to be limiting. In some embodiments the two isomeric forms of the photoisomer component are cis and trans isomers. In some embodiments the transition from the first isomeric form to the second isomeric form is irreversible. In other embodiments the transition from the first isomeric form to the second isomeric form is reversible, as indicated by the dashed arrow 306. The reverse transition may occur in response to optical energy in at least a second wavelength band (as indicated by the label $\lambda_2$) or the reverse transition may occur in response to a reduction or absence of optical energy at least the first wavelength band (as indicated by the label "dark"). The different isomeric forms of the photoisomerizable material can have different biological activities.

Various photosensitive biologically active materials that include photoisomerizable materials are known to those skilled in the art. Some representative examples are as follows; other embodiments will be apparent to those skilled in the art. Volgraf et al, "Allosteric control of an ionotropic glutamate receptor with an optical switch," Nat. Chem. Biol. 2 (2006), 47-52; Banghart et al, "Light-activated ion channels for remote control of neuronal firing," Nature Neuroscience 7 (2004), 1381-1386; and Isacoff et al, "Photoreactive regulator of protein function and methods of use thereof," U.S. Patent Application Publication No. US2007/0128662 A1, all of which are herein incorporated by reference, describe photoisomerizable materials responsive to optical light to regulate protein functions. Kumita et al, "Photo-control of helix content in a short peptide," PNAS 97 (2000), 3803-3808, herein incorporated by reference, describes a peptide modified to include an azobenzene photoisomer and responsive to optical energy to increase the helix content of the peptide.

In some embodiments the photosensitive biologically active material includes a binding partner of a protein, wherein the photosensitive biologically active material is responsive to optical energy to modify an interaction between the binding partner and the protein. The protein and binding partner might be, for example: a receptor and a corresponding receptor ligand (e.g. an agonist, inverse-agonist, antagonist, pore blocker, etc.); an enzyme and a corresponding enzyme ligand (e.g. an allosteric effector, inhibitor, activator, etc.); or any other protein, protein fragment, or protein complex and a corresponding ligand (e.g. an element, molecule, peptide, etc.) capable of binding to the protein, protein fragment, or protein complex and subsequently affecting the behavior of the protein, protein fragment, or protein complex. In some embodiments the binding partner has a probability of binding to the protein that is changeable in response to optical energy in the at least one wavelength band. For example, the photosensitive biologically active material may include a photolabile component that cages or inhibits the binding partner; in response to optical energy, the photolabile component is removed and the binding partner can bind to its corresponding protein. As another example, the photosensitive biologically active material may include a photoisomer, where the isomeric form of the photoisomer affects the ability or the binding partner to bind to its corresponding protein. Volgraf et al, Banghart et al, and Isacoff et al, as cited above, provide examples of a binding partner (e.g. a pore blocker or a receptor agonist) tethered to a photoisomer, where isomerization causes the binding partner to change its position relative to a binding site. In other embodiments a bound combination of the protein and the binding partner has a level of biological activity that is changeable in response to optical energy in the at least one wavelength band. For example, Eisenman et al, "Anticonvulsant and anesthetic effects of a fluorescent neurosteriod analog activated by visible light," Nature Neuroscience 10 (2007), 523-530, herein incorporated by reference, describes a fluorescently-tagged neurosteriod (NBD-allopregnanolone) that binds to the $GABA_A$ receptor and responds to optical light to potentiate receptor function.

In some embodiments, the photosensitive biologically active material includes a combination of a biologically active material and a photosensitive bioactivity-adjusting material, where the photosensitive bioactivity-adjusting material is responsive to optical energy to increase, decrease, or otherwise affect the biological activity of the biologically active material. For example, the photosensitive bioactivity-adjusting material may be disposed to at least partially inhibit biological activity of the biologically active material and responsive to optical energy to at least partially uninhibit biological activity of the biologically active material. Alternatively or additionally, the photosensitive bioactivity-adjusting material may be a material having a first state causing at least a first degree of inhibition of biological activity of the biologically active material and a second state causing at most a second degree of inhibition of biological activity of the biologically active material, where the first degree of inhibition is greater than the second degree of inhibition, and where the photosensitive bioactivity-adjusting material is respon-sive to optical energy in at least the first wavelength band to at least partially convert from an unconverted state to a converted state, the unconverted state and converted state being uniquely selected from the group consisting of the first state and the second state. In some embodiments the conversion from the unconverted state to the converted state may be irreversible. In other embodiments the conversion from the unconverted state to the converted state may be reversible, and the reverse conversion (or reversion) from the converted state to the unconverted state may occur in response to optical energy in at least a second wavelength band or in response to a reduction or absence of optical energy at least the first wavelength band. The biologically active material may include any substance having a biological or pharmaceutical activity, including but not limited to analgesics, anti-infectives, antineoplastics (or other cytotoxic or chemotherapeutic agents), cardiovascular agents, diagnostic agents, dermatological agents, EENT agents, endocrine or metabolic agents, gastrointestinal agents, gynecological agents, hematological agents, immunological agents, neurological agents, psychotherapeutics, pulmonary agents, respiratory agents, or urological agents; also, vitamins, anti-oxidants, and other nutritional or nutriceutical agents. A biologically active material may or may not have an intrinsic response to optical energy to change its biological activity, but the combination of a biologically active material and a photosensitive bioactivity-adjusting material can constitute a photosensitive biologically active material that is responsive to optical energy. Throughout this document, the term "photosensitive biologically active material" is intended to encompass materials that are a combination of a biologically active material and a photosensitive bioactivity-adjusting material, unless context dictates otherwise.

Figure 4A:
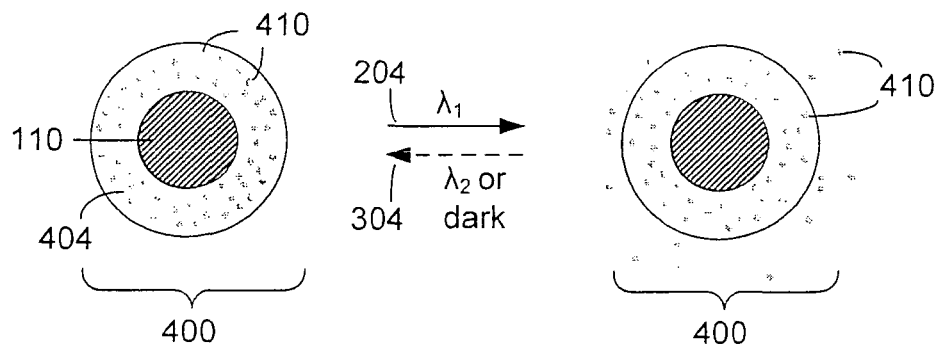
FIGS. 4A-4C depict ionizing-radiation-responsive compositions.
Figure 4B:
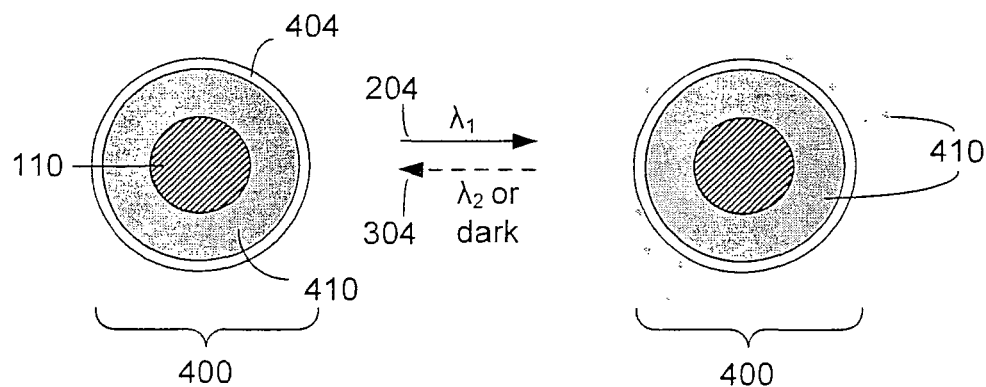
Figure 4C:
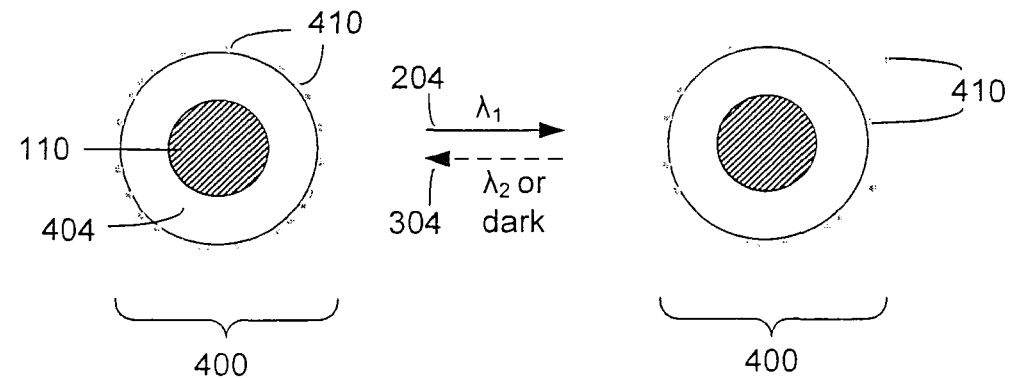

FIGS. 4A-4C depict some exemplary configurations of an ionizing-radiation-responsive composition 400 comprising a luminescent material 110, a photosensitive bioactivity-adjusting material 404, and a biologically active material 410. These are illustrative configurations only, and are not intended to be limiting. FIG. 4A shows a photosensitive bioactivity-adjusting material 404 disposed as a photosensitive matrix material that occupies the interstices between, or otherwise encloses, embeds, or absorbs, a plurality of portions of a biologically active material 410. FIG. 4B shows a photosensitive bioactivity-adjusting material 404 disposed as a photosensitive layer that encloses or envelops a biologically active material 410. FIG. 4C shows a photosensitive bioactivity-adjusting material 404 disposed as a substrate material having a surface that attaches, adsorbs, or otherwise couples to a biologically active material 410. Each configuration in FIGS. 4A-4C depicts a core-shell structure having a core of luminescent material 110, but this is an illustrative disposition of the luminescent material and is not intended to be limiting. In other embodiments of the ionizing-radiation-responsive composition 400, the luminescent material is unattached to either the biologically active material or the photosensitive bioactivity-adjusting material, at least partially attached to one or the other, or variously disposed in configurations that combine all three materials. Some configurations of an ionizing that combine a luminescent material and a photosensitive biologically active material (where the latter may itself comprise a biologically active material and a photosensitive bioactivity-adjusting material) are described elsewhere. In each configuration in FIGS. 4A-4C, the photosensitive bioactivity-adjusting material is responsive to optical energy in at least a first wavelength band, as depicted by the arrow 204 labeled with a wavelength $\lambda_1$, to at least partially allow release of the biologically active material 410. In some embodiments the response to optical energy is irreversible; in other embodiments the response is reversible, as indicated by the dashed arrow 304 depicting a reversion. The reversion may occur in response to optical energy in at least a second wavelength band (as indicated by the label $\lambda_2$) or the reversion may occur in response to a reduction or absence of optical energy at least the first wavelength band (as indicated by the label "dark").

In some embodiments, the photosensitive bioactivity-adjusting material may include a substrate material having a surface that attaches, adsorbs, or otherwise couples to a biologically active material, and responsive to optical energy to release the biologically active material from the surface (optionally, embodiments include a linking agent, e.g. a bifunctional photolytic linker, that connects the substrate material and the biologically active material, and that responds to optical energy to disconnect the substrate material and the biologically active material, e.g. by photolysis). For example, embodiments may use materials such as those in Van Tassel et al and in Lindall (both cited previously and herein incorporated by reference). Various substrate materials include natural polymers, synthetic polymers, silica, glass, quartz, metal, and any other materials capable of directly or indirectly binding to the biologically active material (in some embodiments the luminescent material, or another constituent of the ionizing-radiation-responsive composition, may serve as the substrate material). Various linking agents include 2-nitrophenyl groups, acridines, nitroaromatics, arylsulfonamides, or similar photolytic agents capable of directly or indirectly binding to both the substrate material and the biologically active material.

In some embodiments, the photosensitive bioactivity-adjusting material includes a material that responds to optical energy to change a diffusion characteristic of the material, which may affect a rate of diffusion of the biologically active material through the photosensitive bioactivity-adjusting material. For example, embodiments may use materials such as those in Fink et al, "Photoactivated drug therapy," U.S. Patent Application Publication No. 2003/0216284, herein incorporated by reference; in this reference, optical energy (in the form of a resonant mode of a cavity) causes a change in a diffusion characteristic of at least one component of the cavity, in turn causing release of a pharmaceutical from the cavity (in one embodiment described therein, the at least one component is a polymeric material and the resonance causes heating whereby the polymeric material exceeds a glass transition temperature).

In some embodiments, the photosensitive bioactivity-adjusting material may include a material that responds to optical energy to undergo a shape change (e.g. an expansion, contraction, or bending); the shape change may correspond to a change of a diffusion characteristic, or the shape change may affect some other means for release of the biologically active material (e.g. a shrinkage may create a pressure that expels the biologically active material, or a bending may open a gate-like structure to release the biologically active material), or both. For example, embodiments may use materials such as those in Rosenthal et al, "Triggered release hydrogel drug delivery system," U.S. Pat. No. 7,066,904, herein incorporated by reference; this reference describes catheters that include a polymer or polymer gel disposed to incorporate and immobilize a drug, and responsive to optical light to swell or contract such that the drug is released. Embodiments may use a light-sensitive copolymer or copolymer gel, where a first component of the light-sensitive copolymer or copolymer gel is polyacrylamide, poly(N-isopropylacrylamide), hydroxyethyl methacrylate, dihydroxypropyl methacrylate, a copolymer or mixture thereof, or the like, and a second component of the light-sensitive copolymer or copolymer gel is a light-sensitive compound that induces swelling (as with malachite green derivatives, leucocyanides, leucohydroxides, or similar compounds, e.g. as described in "Photoinduced phase transition of gels," Macromolecules 23 (1990), 1517-1519, herein incorporated by reference, and in Guillet et al, supra) or that induces contraction (as with chlorophyllin, rhodamine, or similar compounds, e.g. as described in "Phase transition in polymer gels induced by visible light," Nature 346 (1990), 345-347, herein incorporated by reference) of the light-sensitive copolymer or copolymer gel in response to optical energy.

In some embodiments, the photosensitive bioactivity-adjusting material may include a material that responds to optical energy to at least partially photodegrade, photodissociate, or photodisintegrate (such terms may be used interchangeably); the photodegradation, photodissociation, or photodisintegration may correspond to a change of a diffusion characteristic, or affect some other means for release of the biologically active material (e.g. a mechanical disintegration of the photosensitive bioactivity-adjusting material may cause an exposure or dispersal of the biologically active material), or both. For example, embodiments may use photochemically degradable polymers such as those described in Guillet et al, supra (e.g. copolymers of ethylenically unsaturated monomers with unsaturated ketones).

In some embodiments, the photosensitive bioactivity-adjusting material may include a material that responds to optical energy to change its hydrophobicity, hydrophilicity, or amphiphilicity; this change may correspond to a change of a diffusion characteristic, or affect some other means for release of the biologically active material (e.g. the change may compel a phase separation of immiscible hydrophilic and hydrophobic components), or both. For example, embodiments may use polymers that convert photochemically from a hydrophobic form to a hydrophilic form, such as those described in Guillet et al, supra (e.g. polymers incorporating a t-butyl ketone group in a side chain immediately adjacent to the polymer backbone).

Figure 5A:
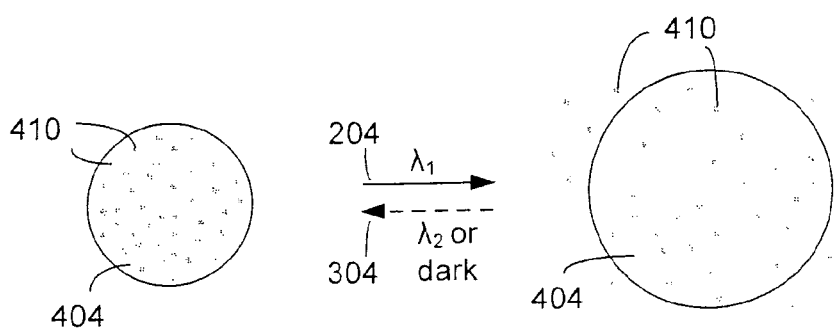
Figure 5B:
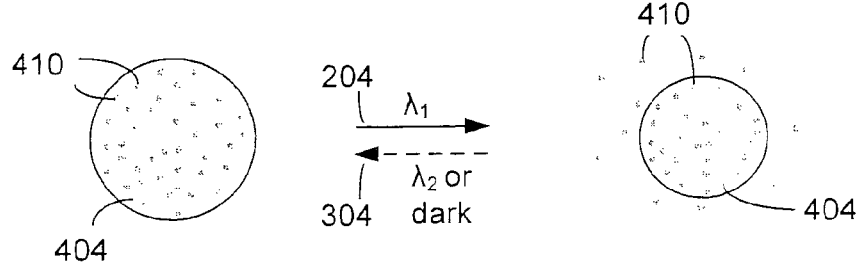
Figure 5C:
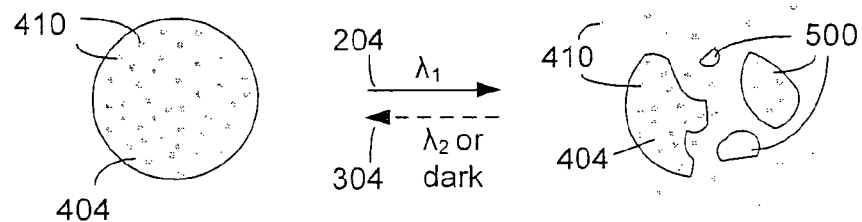

With reference now to FIGS. 5A-5C, some illustrative examples of the preceding embodiments are shown, including a photosensitive bioactivity-adjusting material 404 and a biologically active material 410. For purposes of clarity, a luminescent material is not depicted in these examples, but this omission is not intended to be limiting, and embodiments provide a luminescent material that is enclosed, attached, or otherwise disposed in a vicinity of the photosensitive bioactivity-adjusting material and/or the biologically active material. FIG. 5A depicts an example of a photosensitive bioactivity-adjusting material 404 disposed as a photosensitive matrix material enclosing a biologically active material 410, and responsive to optical energy in at least a first wavelength band (as depicted by the arrow 204 labeled with a wavelength $\lambda_1$) to expand, the expansion causing a release (e.g. by diffusion) of the biologically active material 410. FIG. 5B depicts an example of a photosensitive bioactivity-adjusting material 404 disposed as a photosensitive matrix material enclosing a biologically active material 410, and responsive to optical energy in at least a first wavelength band (as depicted by the arrow 204 labeled with a wavelength $\lambda_1$) to contract, the contraction causing a release (e.g. by pressure expulsion) of the biologically active material 410. Alternatively or additionally, in relation to FIG. 5B, the photosensitive matrix material may be initially disposed to at least partially allow release (e.g. by diffusion) of the biologically active material, and responsive to optical energy to contract, the contraction at least partially inhibiting release (e.g. by reducing diffusion)

of the biologically active material. FIG. 5C depicts an example of a photosensitive bioactivity-adjusting material 404 disposed as a photosensitive matrix material enclosing a biologically active material 410, and responsive to optical energy in at least a first wavelength band (as depicted by the arrow 204 labeled with a wavelength $\lambda_1$) to at least partially photodegrade, photodissociate, or photodisintegrate, thereby releasing the biologically active material 410 (and optionally releasing fragments 500 of the photosensitive bioactivity-adjusting material). In some embodiments, a process depicted in FIGS. 5A-5C is irreversible; in other embodiments the process is reversible, as indicated by the dashed arrow 304 depicting a reverse process. The reverse process may occur in response to optical energy in at least a second wavelength band (as indicated by the label $\lambda_2$) or the reverse process may occur in response to a reduction or absence of optical energy at least the first wavelength band (as indicated by the label "dark").

In some embodiments, the photosensitive bioactivity-adjusting material may include a photosensitive layer (or a plurality thereof) disposed to at least partially enclose or envelop at least a portion of the biologically active material, and responsive to optical energy to at least partially allow release of the biologically active material. The term "layer" is intended to encompass a variety of structures including membranes, films, coatings, shells, coverings, patches, etc., as well as multi-layered structures. The term "layer" further encompasses micelles, vesicles, liposomes, lipid membranes, and other monolayers, bilayers, etc. as assembled from phospholipids, amphiphilic block copolymers, or other amphiphiles. In some embodiments the photosensitive layer may include one or more materials such as those described supra, e.g. a material that responds to optical energy to change a diffusion characteristic, a material that responds to optical energy to undergo a shape change (e.g. an expansion, contraction, or bending), a material that responds to optical energy to at least partially photodegrade, photodissociate, or photodisintegrate (thereby rupturing, perforating, or otherwise disrupting the layer), or a material that responds to optical energy to change its hydrophobicity, hydrophilicity, or amphiphilicity. Embodiments may use a photosensitive layer that embeds one or more light-sensitive channel proteins such as those described in Kocer et al, "A light-actuated nanovalve derived from a channel protein." Science 309 (2005), 755-758, and Kocer et al, "Modified MscL protein channel," U.S. Patent Application Publication No. US2006/0258587, both herein incorporated by reference; these references describe a modified channel protein embedded in a membrane and responsive to optical energy to irreversibly open (or reversibly open/close) a pore in the membrane. Other embodiments may use materials such as those described in P. Ball. "Light pumps drugs from nanoparticles," Nanozone News, Jun. 9, 2005, herein incorporated by reference; e.g., a liposomal membrane (or similar monolayer/bilayer/etc.) that is at least partially comprised of photoisomerizable phospholipids (or similar photoisomizable amphiphiles), or that incorporates photoisomerizable cholesterol (or other photoisomerizable molecules that can attach to or embed within the membrane, e.g. integral membrane proteins), or both, whereby the photosensitive layer responds to optical energy to change porosity (e.g. open pores), become ruptured or perforated, or otherwise allow release of the enclosed biologically active material.

With reference now to FIGS. 6A-6C, some illustrative examples of the preceding embodiments are shown, including a biologically active material 410 and a photosensitive bioactivity-adjusting material 404 disposed as a photosensitive layer that encloses the biologically active material. For purposes of clarity, a luminescent material is not depicted in these examples, but this omission is not intended to be limiting, and embodiments provide a luminescent material that is enclosed, attached, or otherwise disposed in a vicinity of the photosensitive bioactivity-adjusting material and/or the biologically active material. FIG. 6A depicts an example of a photosensitive layer that is responsive to optical energy in at least a first wavelength band (as depicted by the arrow 204 labeled with a wavelength $\lambda_1$) to become ruptured or perforated, whereby the biologically active material is released through one or more ruptured or perforated areas 600. FIG. 6B depicts an example of a photosensitive layer embedding one or more pore-like structures (e.g. channel proteins) in a closed configuration 602, the one or more pore-like structures being responsive to optical energy in at least a first wavelength band (as depicted by the arrow 204 labeled with a wavelength $\lambda_1$) to convert to an open configuration 604, whereby the biologically active material is released. FIG. 6C depicts an example of a photosensitive layer that embeds one or more photoisomerizable molecules (e.g. photoisomerizable phospholipids or cholesterols) in a first isomeric form 606, the one or more photoisomerizable molecules being responsive to optical energy in at least a first wavelength band (as depicted by the arrow 204 labeled with a wavelength $\lambda_1$) to convert to a second isomeric form 608, thereby changing a diffusion, porosity, or other characteristic of the photosensitive layer to allow release of the biologically active material. In some embodiments, a process depicted in FIGS. 6A-6C is irreversible; in other embodiments the process is reversible, as indicated by the dashed arrows 304 depicting a reverse process. The reverse process may occur in response to optical energy in at least a second wavelength band (as indicated by the label $\lambda_2$) or the reverse process may occur in response to a reduction or absence of optical energy at least the first wavelength band (as indicated by the label "dark").

Treating a tissue or lesion with a photosensitive biologically active material typically involves locally irradiating the tissue or region with optical light (or otherwise locally applying some form of optical energy). Optical light or optical energy generally includes electromagnetic radiation in the visible portion of the electromagnetic spectrum (e.g. having wavelengths in the range of 380 nm to 750 nm or frequencies in the range of 400 to 800 THz) as well as neighboring regions of the electromagnetic spectrum (including but not limited to far-infrared, infrared, near-infrared, near-ultraviolet, ultraviolet, and extreme-ultraviolet). The terms "optical light" and "optical energy" also encompass quantized electromagnetic radiation (i.e. photons) and non-radiative forms of electromagnetic energy (e.g. standing waves, evanescent fields, Forster resonance energy transfer (FRET), etc.). Optical light in the red and near-infrared region of the spectrum (the most penetrating) has a penetration depth of about 2 to 6 mm, depending on the wavelength and the tissue. The challenge of delivering optical light to a non-superficial region is therefore a substantial limitation of existing therapies, often involving interstitial, intracavitary, or intravascular placement of optical fibers capped with diffuser tips and coupled to a laser light source. Some embodiments offer an alternate mode of optical light delivery, wherein the optical light or optical energy is locally emitted by a luminescent material in response to ionizing radiation, which can be highly penetrative and precisely delivered to a region of interest.

Ionizing radiation is radiation having an ability to ionize an atom or molecule. Radiation may be referred to as ionizing radiation whether or not the radiation causes ionization in any particular embodiment or use of the aspects described herein.

For example, ionizing radiation may have energy sufficient to ionize a first kind of atom or molecule, but insufficient to ionize a second kind of atom or molecule. Therefore, in some embodiments where the ionizing radiation interacts only with the second kind of atom or molecule, it may not cause ionization. The ionizing radiation can be electromagnetic radiation such as extreme ultraviolet (EUV) rays, soft or hard x-rays, or gamma-rays, or charged particle radiation in the form of electrons, protons, or ions (e.g., carbon and neon).

The ionizing radiation emitter 100 can include a high-voltage vacuum tube or field emitter, EUV or x-ray laser, discharge- or laser-produced plasma device, synchrotron, particle accelerator, or similar device; or, a radioactive material comprising one or more radioactive isotopes; or, a combination of such materials and/or devices. If the ionizing radiation emitter includes a radioactive isotope, the ionizing radiation may be a direct radioactive decay product (e.g. an electron, position, or gamma ray), or a product of a subsequent process (e.g. bremsstrahlung or characteristic x-rays, gamma rays from electron-positron annihilation, or electrons created by photoelectric, Auger, or pair production processes).

If the region 104 includes a human or animal patient or a portion thereof, the ionizing radiation emitter can be positioned outside, adjacent to, or inside the patient. Examples of ionizing radiation emitters that can be positioned outside the patient include x-ray radiograph instruments, computed tomography (CT) instruments, fluoroscopes, radiosurgery instruments (such as the Cyberknife or Gamma Knife), teletherapy or external beam radiotherapy devices, and proton or ion beam devices. Examples of ionizing radiation emitters that can be positioned adjacent to or inside the patient include catheter-mounted miniaturized x-ray tubes, sealed radioactive sources that are applied as molds or implanted by surgery, catheter, or applicator; and radiopharmaceuticals that are directly injected or ingested (these include beta-active isotopes of iodine, phosphorus, etc. as used for radiotherapy, gamma-active isotopes of gallium, technetium, etc. as used for imaging, and positron-emitting isotopes of carbon, fluorine, etc. as used for positron-emission tomography (PET)).

In various embodiments the ionizing radiation 102 can be substantially monochromatic, quasi-monochromatic, or polychromatic. Examples of substantially monochromatic or quasi-monochromatic ionizing radiation include characteristic x-rays, beta and gamma rays from radioactive decay, undulator synchrotron rays, and accelerated proton or ion beams. Examples of polychromatic ionizing radiation include wiggler and bending magnet synchrotron rays and bremsstrahlung rays. The energy spectrum and intensity of the ionizing radiation can be modified, shaped, or varied in time by various means known to those skilled in the art; for example, by adjusting the cathode-anode voltage in an x-ray vacuum tube, or using x-ray optics devices such as Bragg monochromators and attenuation filters.

Various embodiments utilize different space and time configurations of the ionizing radiation 102. The particular depictions of the ionizing radiation that are shown in the figures are schematic and not intended to be limiting. For example, the ionizing radiation may be substantially isotropic (i.e. radiating in most or all directions), fan-shaped, cone-shaped, collimated in a thin ray, etc.; these and other irradiation patterns can be achieved by various means known to those skilled in the art, e.g. deployment of lenses, mirrors, zone plates, baffles, slots, or apertures, or positioning of leaves in a multileaf collimator (MLC). In those embodiments where the ionizing radiation is deployed as a beam, the orientation and position of the beam can be varied with respect to the target region 104, for example by mounting the emitter and/or the target on a moveable pivot, track, arm, or gantry, or manually adjusting the position of an intravascular catheter with an emitter on its distal end. The extent of the irradiated region 106 is determined by the energy, intensity, shape, orientation, and position of the ionizing radiation beam, and by the scattering and absorption properties of the region 104. For example, depth-dose characteristics of typical radiotherapy x-ray and proton beams are described in A. Boyer et al, "Radiation in the Treatment of Cancer," *Physics Today*, September 2002, which is herein incorporated by reference. Typically, hard x-rays are more penetrating than soft x-rays, and protons have a longer range than electrons, with a characteristic Bragg peak at the end of their range. In some embodiments the irradiation may comprise multiple ionizing radiation beams, either emitted in a time sequence by a single emitter, or emitted by a plurality of emitters, or both. The multiple beams may have different energies, intensities, orientations, and/or positions; alternatively, a continuously or stroboscopically emitting beam (or a plurality thereof) may continuously or intermittently change its energy, intensity, orientation, and/or position. In some embodiments, techniques such as those used in radiotherapy and stereotactic radiosurgery can be utilized to deliver an effective amount of radiation to a region of therapeutic interest (such as a tumor) while reducing radiation damage to neighboring tissues; these techniques include 3D conformal radiotherapy (3DCRT) and intensity-modulated radiotherapy (IMRT), as described in A. Boyer, "The Physics of Intensity-Modulated Radiation Therapy," *Physics Today*, September 2002, which is herein incorporated by reference.

The luminescent material 110 is a material that is responsive to ionizing radiation to produce optical energy. Generally, the term "luminescent material" encompasses all materials that respond to radiation (ionizing or non-ionizing) to produce optical energy (the term "phosphor" is sometimes used with equivalent meaning), and it produces the optical energy by a process called luminescence. The term "luminescence" encompasses various processes including fluorescence, phosphorescence, and afterglow. Many luminescent materials are known to those skilled in the art, with various characteristics of absorption, emission, and efficiency, for example as described in G. Blasse and B. C. Grabmaier, *Luminescent Materials*, Springer-Verlag, Berlin 1994, which is herein incorporated by reference.

When the incident radiation is ionizing radiation, the luminescent material is often referred to as a scintillator. Scintillators can comprise organic or inorganic materials, in the form of crystals (including micro- and nano-scale crystals), particles (including micro- and nano-scale particles), powders, composites, ceramics, glasses, plastics, liquids, and gases. Some scintillation materials and detectors are described in M. Nikl, "Scintillation detectors for x-rays," Meas. Sci. Technol. 17 (2006), R37-R54 and in C. W. E. van Eijk, "Inorganic scintillators in medical imaging," Phys. Med. Biol. 47 (2002), R85-R106, which are both herein incorporated by reference. Scintillators are sometimes referred to as phosphors, especially in applications where the material is deployed as a powder screen, viz. lamp phosphors, cathode ray tube (CRT) phosphors, x-ray intensifying screen phosphors, and x-ray storage phosphors (c.f. G. Blasse and B. C. Grabmaier, supra; storage phosphors are additionally described in H. von Seggern, "Photostimulable x-ray storage phosphors: a review of present understanding," Braz. J. Phys. 29 (1999), 254-268, and in W. Chen, "Nanophase luminescence particulate material," U.S. Pat. No. 7,067,072, which are both herein incorporated by reference).

A luminescent material generally comprises one or more sensitizers and/or one or more activators embedded in a host material, although in some cases an activator also plays the role of sensitizer, or the host material plays the role of sensitizer or activator or both. The luminescence process generally proceeds as follows: (1) incident radiation is absorbed by the sensitizer; (2) the energy is transferred through the host material to the activator, raising it to an excited state; and (3) the activator returns to the ground state by emission of optical radiation. A first example is the lamp phosphor $Ca_5(PO_4)_3F$: $Sb^{3+}$, $Mn^{2+}$, where an $Sb^{3+}$ sensitizer/activator and an $Mn^{2+}$ activator are embedded as dopants in a fluorapatite host material. A second example is described in Y. L. Soo et al, "X-ray excited luminescence and local structures in Tb-doped $Y_2O_3$ nanocrystals," J. Appl. Phys. 83 (1998), 5404-5409, which is herein incorporated by reference; in this material, the yttrium in the host nanocrystal is a sensitizer, and the dopant terbium is a sensitizer/activator with green luminescence. A third example is a class of organometallic lanthanide-cryptate scintillators described in G. Blasse et al, "X-ray excited luminescence of samarium(III), europium(III), gadolinium(III), and terbium(III) 2.2.1 cryptates," Chem. Phys. Lett. 158 (1989), 504-508, which is herein incorporated by reference; in these materials, the cryptate bypyridine is a sensitizer, and the caged lanthanide is a sensitizer/activator. A fourth example is the x-ray phosphor described in W. Chen et al, "The origin of x-ray luminescence from CdTe nanoparticles in CdTe/BaFBr:$Eu^{2+}$ nanocomposite phosphors," J. Appl. Phys. 99 (2006), 034302, which is herein incorporated by reference; in this material, the BaFBr host material is a sensitizer, the $Eu^{2+}$ dopant is a sensitizer/activator emitting at 390 nm, and the CdTe nanoparticle is an activator emitting at a wavelength of 541, 610, or 650 nm for a nanoparticle size of 2, 4, or 6 nm, respectively.

The absorption of incident radiation by a sensitizer (or a host material component acting as a sensitizer) generally varies with the energy of the incident radiation according to a characteristic absorption spectrum; some embodiments provide a plurality of sensitizers (or a plurality of host material components acting as sensitizers, or a combination thereof) having a plurality of characteristic absorption spectra. The emission of radiation by an activator (or a host material component acting as an activator) generally varies with the energy of the emitted radiation according to a characteristic emission spectrum; some embodiments provide a plurality of activators (or a plurality of host material components acting as activators, or a combination thereof) having a plurality of characteristic emission spectra. In some embodiments, selective transfer of energy from the plurality of sensitizers to the plurality of activators (e.g. as characterized by a matrix of energy transfer efficiencies) can be used to provide selective wavelength/energy conversion of incident radiation to emitted radiation; viz, incident radiation in a first (second) absorption energy band substantially excites a first (second) sensitizer, the excitation energy is substantially transferred to a first (second) activator, and the first (second) activator substantially emits radiation in a first (second) emission energy band.

The overall effectiveness of the luminescent material for converting incident ionizing radiation into optical energy is determined in part by the absorption characteristics of the material. Absorption of ionizing radiation in matter, and detection thereof, are described in W. M. Yao et al, *Review of Particle Physics*, J. Phys. G: Nucl. Part. Phys. 33 (2006), 258-292, which is herein incorporated by reference. If the ionizing radiation consists of charged particles (including electrons, protons, and ions), the charged particles lose energy through Coulomb interactions with the electrons in the material; ionization is the dominant Coulomb process except at ultrarelativistic energies. A material with a high electron density (i.e. a high mass density) is typically a better absorber of charged particle radiation. If the ionizing radiation consists of photons (ultraviolet rays, x-rays, or gamma rays), absorption is dominated by the photoelectric effect at low energies, then by Compton and pair production processes at successively higher energies. For Compton and pair production processes, the absorption is proportional to electron density, and a material with a high electron density (i.e. a high mass density) is a better absorber. For the photoelectric effect, the absorption cross section is approximately proportional to $Z^3/E^3$, where E is the energy of the incident photon and Z is the atomic number of the target atom. A material with a high effective atomic number $Z_{eff}$ (i.e. as averaged over its constituent elements) is therefore a better photoelectric absorber. Overall, a material with a high mass density, and a high effective atomic number $Z_{eff}$, is a better absorber of both charged particle energy and photon energy.

Moreover, the photoelectric cross section is characterized by discontinues, known as absorption edges, as thresholds for ionization of various atomic shells are reached. The absorption edges for successive shells with principal quantum numbers n=1, n=2, n=3, etc. are respectively called the K-edge, L-edge, M-edge, etc. In some embodiments, the ionizing radiation includes one or more substantially monochromatic beams of photons, each having an energy E just above a photoelectric absorption edge of the luminescent material; or, the ionizing radiation includes a polychromatic beam of photons, where the energy spectrum of the polychromatic beam consists essentially of a plurality of peaks coinciding with a plurality of absorption edges for the luminescent material. In these embodiments the ionizing radiation is substantially absorbed by the luminescent material, and the absorption by neighboring tissues may be mitigated, especially in those embodiments where the absorption edges of the luminescent material are distinct from those of the neighboring tissues.

In some embodiments, the luminescent material has a host material that includes a heavy metal selected from the group consisting of alkaline metals, alkaline earth metals, transition metals, poor metals, and metalloids. The term "heavy metal" is taken to include any metal or metalloid element having an atomic number greater than or equal to 37 (i.e. elements in periods 5, 6, or 7). The term "alkaline metals" is taken to include elements in group 1 of the periodic table (excluding hydrogen), i.e. lithium, sodium, potassium, rubidium, cesium, and francium. The term "alkaline earth metals" is taken to include elements in group 2 of the period table, i.e. beryllium, magnesium, calcium, strontium, barium, and radium. The term "transition metals" is taken to include elements in groups 3 to 12 of the periodic table. The term "poor metals" is taken to include aluminum, gallium, indium, tin, thallium, lead, and bismuth. The term "metalloids" is taken to include boron, silicon, germanium, arsenic, antimony, tellurium, and polonium.

In some embodiments, the emission spectrum of the luminescent material should substantially overlap or coincide with the absorption spectrum of the photosensitive biologically active material. The emission spectrum is partially determined by intrinsic properties of the activator component of the luminescent material, and by its local environment in the host material (e.g. the activator's crystal field, coordination, chelation, etc.). If the luminescent material comprises nanoparticles or nanocrystals, a quantum size effect can occur, whereby the spatial confinement of the valence electron wavefunctions causes smaller particles of the same composition to have emission spectra that are shifted to smaller wavelengths (e.g. as observed in W. Chen et al, supra).

In some embodiments, the luminescent material can include quantum dots. These are nanocrystals comprised of various semiconductor materials, which can include but are not limited to group IV elements (C, Si, Ge), group IV binary compounds (SiC, SiGe), III-V binary compounds (AlSb, AlAs, AlN, AlP, BN, BP, BAs, GaSb, GaAs, GaN, GaP, InSb, InAs, InN, InP, etc.), III-V ternary compounds (AlGaAs, InGaAs, AlInAs, AlInSb, GaAsN, GaAsP, AlGaN, AlGaP, InGaN, InAsSb, InGaSb, etc.), III-V quaternary compounds (AlGaInP, AlGaAsP, InGaAsP, AlInAsP, AlGaAsN, InGaAsN, InAlAsN, etc.), III-V quinary compounds (GaInNAsSb), II-VI binary compounds (CdSe, CdS, CdTe, ZnO, ZnSe, ZnTe, etc.), II-VI ternary compounds (CdZnTe, HgCdTe, HgZnTe, HgZnSe, etc.), I-VII binary compounds (CuCl, etc.), IV-VI binary compounds (PbSe, PbS, PbTe, SnS, SnTe, etc.), IV-VI ternary compounds (PbSnTe, $Tl_2SnTe_5$, $Tl_2GeTe_5$, etc.), V-VI binary compounds ($Bi_2Te_3$, $Bi_2S_3$ etc.), II-V binary compounds ($Cd_3P_2$, $Cd_3As_2$, $Cd_3Sb_2$, $Zn_3P_2$, $Zn_3As_2$, $Zn_3Sb_2$, etc.), miscellaneous oxides ($TiO_2$, $Cu_2O$, CuO, $UO_2$, $UO_3$, etc.), other miscellaneous inorganic compounds ($PbI_2$, $MoS_2$, GaSe, CuInGaSe, PtSi, $BiI_3$, $HgI_2$, TlBr, etc.), and organic semiconductors. In some embodiments, the quantum dots comprise heavier elements such as mercury, lead, bismuth, or polonium, to enhance the absorption of ionizing radiation. The quantum dots can also be doped, e.g. as described in Erwin et al, "Doping semiconductor nanocrystals," Nature 436 (2005), 91-94, which is herein incorporated by reference; accordingly some embodiments provide quantum dots that are doped with heavier elements, such as the lanthanides or other period 6 elements, again to enhance the absorption of ionizing radiation. In some embodiments the quantum dots may have a core-shell structure, with the core consisting of a first semiconductor material, and a shell consisting of a second semiconductor material. Additionally, one or more coatings and/or functional groups may be applied or attached to the quantum dot, to improve solubility, durability, suspension characteristics, bioactivity, etc. as discussed infra. Desired optical properties of the quantum dot (e.g. quantum efficiency, Stokes shift, emission wavelength) can be further adjusted by controlling the size, shape, and structure of the quantum dot through various fabrication processes known to those skilled in the art (for example, W. Chen, supra, describes how to control the emission wavelength by adjusting the nanoparticle size; accordingly, the emission wavelength can be matched to a peak in the absorption spectrum of the photosensitive biologically active material).

Figure 7:
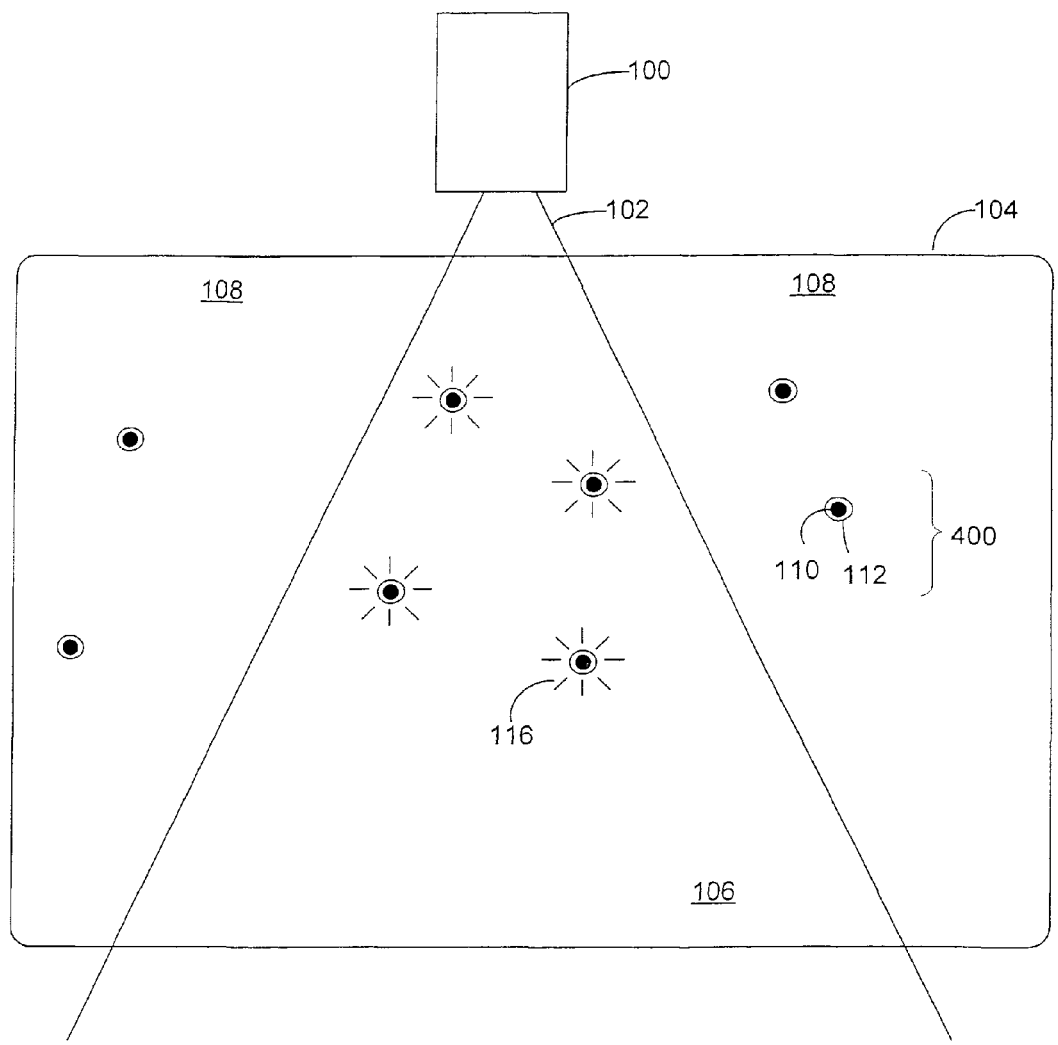
FIG. 7 depicts irradiation of an ionizing-radiation-responsive composition.
Figure 8A:
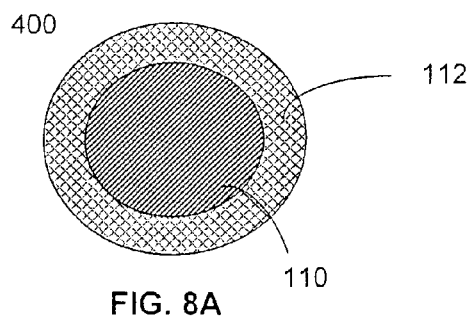
Figure 8B:
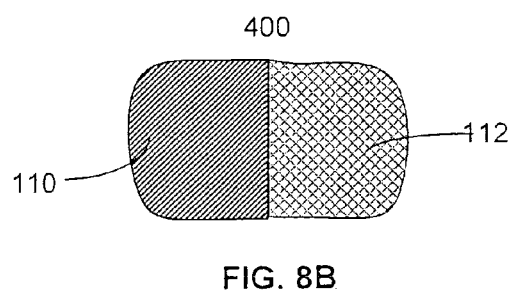
Figure 8C:
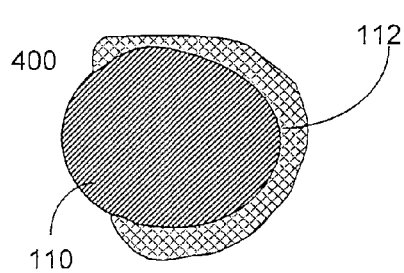
Figure 8D:
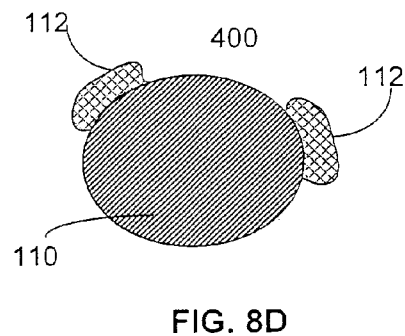
Figure 8E:
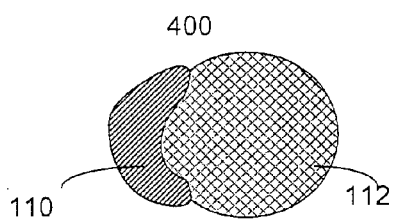
Figure 8F:
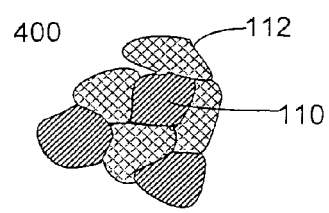
Figure 8G:
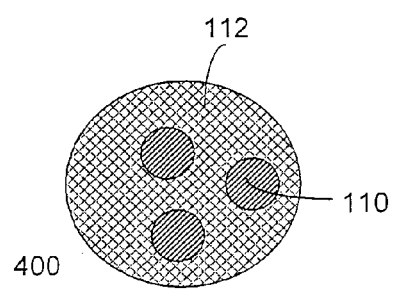
Figure 9A:
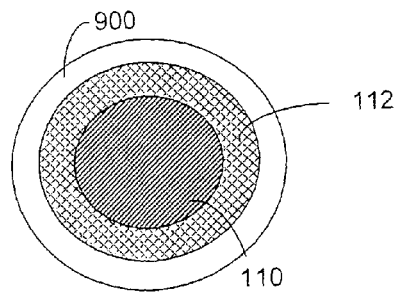
Figure 9B:
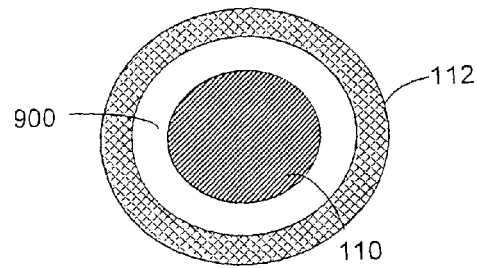
Figure 9C:
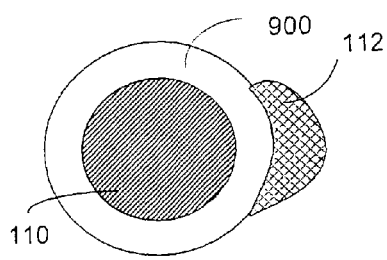
Figure 9D:
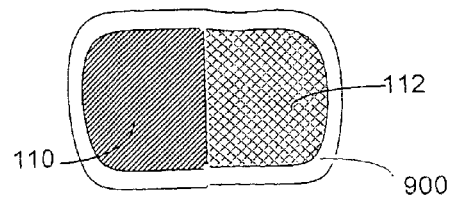
Figure 9E:
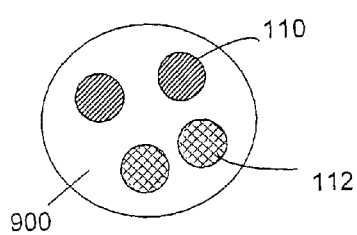
Figure 9F:
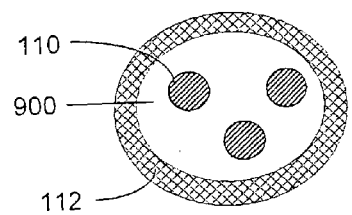
Figure 9G:
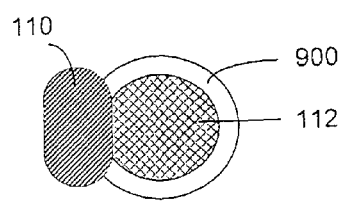
Figure 9H:
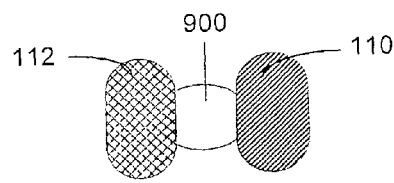

FIG. 7 depicts another illustrative embodiment and use in which an ionizing radiation emitter 100 emits an ionizing radiation 102. The ionizing radiation irradiates at least a portion of a region 104 that contains a ionizing-radiation-responsive composition 400, which is a bound composition comprising a luminescent material 110 and a photosensitive biologically active material 112. As in FIG. 1, the luminescent material responds to ionizing radiation to produce optical energy, and the photosensitive biologically active material responds to optical energy to become biologically active, as indicated schematically by the radial lines 116 (other embodiments provide other responses of the photosensitive biologically active material; for example, the photosensitive biologically active material may respond to the optical energy to become biologically inactive, to partially increase or decrease a level of biological activity, to change from a first mode of biological activity to second mode of biological activity, etc.).

When the luminescent material and the photosensitive biologically active material are bound together as in FIG. 7, the optical energy may be transferred from the luminescent material to the photosensitive biologically active material by either radiative or nonradiative processes. An example of a nonradiative energy transfer process is Forster resonance energy transfer (FRET), as described in G. Blasse and B. C. Grabmaier, supra.

FIG. 7 illustrates the ionizing-radiation-responsive composition in cross-section as having a core-shell structure, with the core consisting of luminescent material and a shell consisting of photosensitive biologically active material. This is only a schematic depiction of the bound composition and is not intended to be limiting. Some configurations of the bound composition include but are not limited to those depicted in cross section in FIGS. 8A-8G. In various configurations the two materials form a core-shell structure with one material comprising the core and the other material comprising either a complete shell or one or more spots or patches on the surface of the core; a binary aggregate structure with one or more adjoining regions of the two materials; a host-inclusion structure, where one material is an inclusion or dopant of the other material; and other configurations. Various techniques known to those skilled in the art can be used to produce or synthesize these bound compositions. For example, W. Chen and J. Zhang, "Using nanoparticles to enable simultaneous radiation and photodynamic therapies for cancer treatment," J. Nanosci. Nanotech. 6 (2006), 1159-1166, which is herein incorporated by reference describes a conjugation of porphyrins to nanoparticles using L-cysteine as a bifunctional ligand. M. Wieder et al. "Intracellular photodynamic therapy with photosensitizer-nanoparticle conjugates: cancer therapy, using a 'Trojan horse,'" Photochem. Photobiol. Sci. 5 (2006), 797-734 herein incorporated by reference, describes a derivatization of a phthalocyanine photosensitizer with a thiol moiety to provide a direct linkage to a nanoparticle surface via self-assembly. Other functional ligands and conjugation methods are described in G. T. Hermanson, *Bioconjugate Techniques*, Academic Press (1996). L. Shi et al, "Singlet oxygen generation from water-soluble quantum dot-organic dye nanocomposites,", J. Am. Chem. Soc. 128 (2006), 6278-6279, herein incorporated by reference, describes a synthesis of a nanocomposite consisting of meso-tetra(4-sulfonatophenyl)porphine dihydrochloride (TSPP), a photosensitizer, bound to CdTe nanocrystals via electrostatic interaction.

In some embodiments, the ionizing-radiation-responsive composition further comprises an adjuvant matrix or coating material. Some configurations of the bound composition include but are not limited to those depicted in cross section in FIGS. 9A-9H, where the unshaded region 900 represents the adjuvant matrix or coating material. In generals the adjuvant matrix or coating material is a material that is selected and disposed to improve various biological and pharmaceutical characteristics of the ionizing-radiation-responsive composition, including but not limited to solubility, durability, suspension stability, bioactivity, biocompatibility, chemical affinity, biological affinity, porosity, permeability, non-toxicity, and radiation responsiveness. The adjuvant matrix or coating material may also provide a mechanical means to embed, confine, attach, adhere, or bind together at least a portion of the constituents of the ionizing-radiation-responsive composition, or at least partially sustain the proximity of at least a portion of the constituents, either permanently or temporarily (an example of the latter is a slow-release polymer). Generally, a matrix material is a material that at least partially embeds one or more other materials, or at least partially occupies interstices in the spatial configuration of one or more other materials, and a coating material is a material that at least partially surrounds or envelops one or more other materials; however, those of skill in the art will recognize that the terms "matrix material" and "coating material" encompass other configurations, and that in some contexts the terms have overlapping meaning (e.g. a matrix material that is also a coating material, or vice versa). The use of the term "adjuvant" is intended in this context to denote that the adjuvant matrix or coating material is not substantially a photosensitive biologically active material, or substantially a photosensitive bioactivity-adjusting material, nor substantially a luminescent material responsive to ionizing radiation to produce optical energy to activate a photosensitive biologically active material or a photosensitive bioactivity-adjusting material; rather, the adjuvant matrix or coating is a material that potentiates, moderates, improves, or otherwise modifies the individual or cumulative biological or pharmaceutical characteristics of these other constituents of the ionizing-radiation-responsive composition. An adjuvant matrix or coating material is therefore understood to be distinct from a photosensitive bioactivity-adjusting material disposed as a photosensitive matrix or coating. The intended meaning of "matrix" or "coating" (e.g. photosensitive matrix or adjuvant matrix) will be apparent from the context in which said term is used Various adjuvant matrix and coating materials, and methods of deploying such materials in a bound composition, are known to those skilled in the art. Some representative examples are as follows; other embodiments will be apparent to those skilled in the art. A first example is a porous glass, such as that used to embed CdSe/ZnS quantum dot alpha particle scintillators as described in S. E. Letant and T. F. Wang, "Study of porous glass doped with quantum dots or laser dyes under alpha irradiation,", Appl. Phys. Lett. 88 (2006), 103110, herein incorporated by reference. A second example is a silica shell, which can enclose a photosensitizer as described in Wang et al, "Nanomaterials and singlet oxygen photosensitizers: potential applications in photodynamic therapy," J. Mater. Chem. 14 (2004), 487-493; E. Bergey and P. Prasad, "Small spheres, big potential," OE Magazine, Jul. 2003, 26-29; and P. Prasad et al, "Ceramic based nanoparticles for entrapping therapeutic agents for photodynamic therapy and method of using same," U.S. Patent App. Pub. No. US 2004/0180096; which publications are herein incorporated by reference. The silica shell can be made hydrophobic, hydrophilic, or both, as appropriate for biological context, and the porosity of the silica shell can be tailored, e.g. to allow permeation of singlet oxygen from a photosensitizer. Silica shells can also be used to coat quantum dots (cf. X. Michalet, "Quantum dots for live cells, in vivo imaging, and diagnostics," Science 307 (2005), 538-544, herein incorporated by reference), magnetic nanoparticles (c.f. L. Levy et al, "Nanochemistry: synthesis and characterization of multifunctional nanoclinics for biological applications," Chem. Mater. 14 (2002), 3715-3721; B. A. Holm et al, "Nanotechnology in biomedical applications," Mol. Cryst. Liq. Cryst. 374 (2002), 589-598; and P. Prasad et al, "Magnetic nanoparticles for selective therapy," U.S. Pat. No. 6,514,481; which publications are herein incorporated by reference), and other particles or nanoparticles, and they can be functionalized with PEG groups for enhanced biocompatibility, e.g. as described in T. Zhang et al, "Cellular effect of high doses of silica-coated quantum dot profiled with high throughput gene expression analysis and high content cellomics measurements," Nano Letters 6 (2006), 800-808, herein incorporated by reference. A third example is a micellular agent such as PEG-PE, which can be used, for example, to encapsulate a photosensitizer (cf. A. Roby, et al, "Solubilization of poorly soluble PDT agent, meso-tetraphenylporphin, in plain or immunotargeted PEG-PE micelles results in dramatically improved cancer cell killing in Vitro," Eur. J. Pharm. Biopharm. 62 (2006), 235-240, herein incorporated by reference) or a quantum dot (c.f. B. Dubertret et al, "In vivo imaging of quantum dots encapsulated in phospholipid micelles," Science 298 (2002), 1759-1762, herein incorporated by reference). A fourth example is a matrix material comprising polyacrylamide hydrogel, sol gel silica, or cross-linked decyl methacrylate; nanoparticles utilizing these matrix materials are described in E. Monson et al, "PEBBLE nanosensors for in vitro bioanalysis," Biomedical Photonics Handbook, CRC Press, 2003, 59.1-59.14; "Nanotechnology tackles brain cancer," Monthly Feature, December 2005, NCI Alliance for Nanotechnology in Cancer; and "Watery nanoparticles deliver anticancer therapy," Nanotech News, Mar. 5, 2007, NCI Alliance for Nanotechnology in Cancer; which publications are herein incorporated by reference. A fifth example is a chelant material (either a natural chelant such as a porphyrin or porphyrin derivative, or a synthetic chelant such as ethylenediaminetetraacedit acid (EDTA) or diethylenetriaminepentaacetic acid (DTPA)) or cryptand material (such as bypiridine), which materials can form a coordination complex to enclose various substrates including metals and cations. A sixth example is a fullerene or a fullerene derivative (e.g. a carbon nanotube or buckyball), where the interior volume can be used to contain various materials; for example, B. Sitharaman et al, "Superparamagnetic gadonanotubes are high-performance MRI contrast agents," Chem. Commn. (2005), 3915-3917, herein incorporated by reference, describes a carbon nanotube loaded with $Gd^{3+}$ ions as an MRI contrast agent.

Because a photosensitive biologically active material can be undesirably activated by ambient optical energy such as sunlight, special procedures are sometimes necessary to avoid undesirable activation during storage, administration, treatment, and post-treatment. For example, patients treated with the photosensitizing drug porfimer sodium are instructed to avoid sunlight or bright indoor light for at least 30 days after treatment. In some embodiments, the ionizing-radiation-responsive composition includes an optically-inhibiting material disposed to at least partially block coupling of optical energy to the photosensitive biologically active material. In an embodiment, the optically-inhibiting material is disposed to selectively block coupling of optical energy from sources other than the luminescent material. In such an embodiment, the ionizing-radiation-responsive composition can become biologically active when irradiated with ionizing radiation, but the optically-inhibiting material may at least partially prevent the composition from becoming biologically active when irradiated with optical energy. This can simplify storage, administration, and treatment procedures, and mitigate any ambient light photosensitivity of the patient. In some embodiments the optically-inhibiting material may comprise one or more thin metallic layers, optionally configured in a mesh or porous structure. Lower-Z metallic elements such as beryllium, aluminum, or titanium may be utilized to provide optical blocking without substantial attenuation of ionizing radiation such as x-rays. In other embodiments the optically-inhibiting material may comprise chromophores that are embedded in the adjuvant matrix or coating material to enhance absorption of optical energy in a wavelength range corresponding to an absorption band of the photosensitive biologically active material. For example, organic dye molecules can be added to a polymer matrix or coating, or various metals (such as cobalt, gold, selenium, copper, etc. and salts, oxides, etc. thereof) can be added to a silica matrix or coating. In other embodiments the optically-inhibiting material may comprise a polymeric photonic band gap material (e.g. as described in Fink et al, "Polymeric photonic band gap materials," U.S. Pat. No. 6,433,931, herein incorporated by reference) having a band gap that at least partially coincides with an absorption band of the photosensitive biologically active material.

In some embodiments the ionizing-radiation-responsive composition further comprises a biotargeting agent conveying a selective biological affinity to the ionizing-radiation-responsive composition. Some configurations of the bound composition include but are not limited to those depicted in cross section in FIGS. 10A and 10B, in which an ionizing-radiation-responsive material 1000 (comprising a luminescent material and a photosensitive biologically active material, and optionally including other materials, e.g. an adjuvant matrix or coating material) is linked to or coated wraith a biotargeting agent 1010. The depictions are schematic and not intended to be limiting. In FIG. 10A, the biotargeting agent 1010 is depicted as having a y-shape, which may suggest an exemplary embodiment in which the biotargeting agent is an antibody; but this is a symbolic depiction that encompasses all biotargeting agents, including but not limited to: proteins and glycoproteins, monoclonal and polyclonal antibodies, lectins, receptor ligands (including but not limited to vitamins, hormones, toxins, and analogues or fragments thereof), peptides and polypeptides, aptamers, polysaccharides, sugars, and various other bioactive ligands and moieties. Various bioconjugation methods are known to those skilled in the art to deploy these biotargeting agents as a component of the ionizing-radiation-responsive composition. For example, W. Chen and J. Zhang, supra describes a use of nanoparticle-conjugated folic acid as a tumor-specific ligand. E. Bergey and P. Prasad, supra, L. Levy et al, supra, and P. Prasad et al, supra, describe an exemplary conjugation of silica-coated nanoparticles with peptides, polypeptides, or leutinizing hormone-releasing hormone (LH-RH). Various illustrative bioconjugations of quantum dots are described in R. Hardman, "A toxicologic review of quantum dots: toxicity depends on physicochemical and environmental factors," Environmental Health Perspectives 114 (2006), 165-172, herein incorporated by reference; S. Weiss et al, "Semiconductor nanocrystal probes for biological applications and process for making and using such probes," U.S. Pat. No. 6,207,392, herein incorporated by reference; and X. Michalet, supra. B. Storrie et al, "B/B-like fragment targeting for the purposes of photodynamic therapy and medical imaging," U.S. Pat. No. 6,631,283, herein incorporated by reference, illustrates the conjugation of a targeting fragment of a toxin molecule or lectin to a photosensitizing or imaging agent. A. Roby et al, supra, and B. Dubertret et al, supra, describe bioconjugations of micelles with antibodies and DNA, respectively. H. Dees and T. Scott, "Method for improved imaging and photodynamic therapy," U.S. Pat. No. 6,493,570, herein incorporated by reference, describes a derivatization of a halogenated xanthene photosensitizer with various targeting moieties.

Some embodiments of the invention provide a first bound composition that includes a photosensitive biologically active material and a first affinity agent, and a second bound composition that includes a luminescent material and a second affinity agent. The first and second affinity agents are any two agents (which may be identical) having a tendency to induce a proximity (e.g. in situ) of the photosensitive biologically active material and the luminescent material, whereby the photosensitive biologically active material may respond to optical energy produced by the luminescent material. In some embodiments the first and second affinity agents may include, respectively, first and second biotargeting agents having first and second selective biological affinities, where the first and second selective biological affinities are at least partially overlapping (e.g. the first and second biotargeting agents each have at least some common affinity for a particular tissue, lesion, organ, or other region, whereby the photosensitive biologically active material and the luminescent material can be brought into proximity in situ). In other embodiments the first and second affinity agents may, include, respectively, first and second binding partners selected from a pair of binding partners. Binding partners are pairs of molecules (or functional groups) having an affinity to bind together. Some examples include: an antigen and a corresponding antibody or fragment thereof; a hapten and a corresponding anti-hapten; biotin and avidin or streptavadin; folic acid and folate binding protein; a hormone and a corresponding hormone receptor; a lectin and a corresponding carbohydrate, and enzyme and a corresponding cofactor, substrate, inhibitor, effector, etc.; vitamin B12 and intrinsic factor; complementary nucleic acid fragments (including DNA, RNA, and PNA (peptide nucleic acid) sequences), an antibody and Protein A or G; a polynucleotide and a corresponding polynucleotide binding protein; other proteins and corresponding ligands; also, various covalent binding pairs such as sulfhydryl reactive groups, amine reactive groups, carbodiimide reactive groups, etc. Various methods are known to those skilled in the art to deploy such binding partners in bound compositions. For example, Amaratunga et al, "Pharmaceuticals for enhanced delivery to disease targets," U.S. Patent Application Pub. No. US2005/0260131, herein incorporated by references, describes pairs of compounds conjugated to complementary oligopeptide sequences (e.g. PNA sequences). Pomato et al, "In vivo binding pair pretargeting," U.S. Pat. No. 5,807,534, herein incorporated by reference, describes methods that deploy an enzyme and a corresponding enzyme inhibitor as a binding pair for in-situ pretargeting of an effector molecule (e.g. a radiometal). Croker et al, "Sol-gel coated glass microspheres for use in bioassay," U.S. Patent Application Pub. No. US 2007/0117089, herein incorporated by reference, describes glass microspheres with a sol-gel coating that comprises a bioactive probe, where the bioactive probe can include one binding partner selected from a pair of binding partners.

Figure 11A:
Figure 11B:
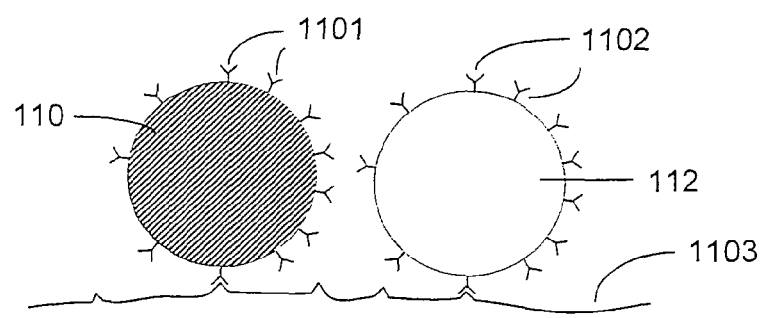
Figure 11C:
Figure 11D:
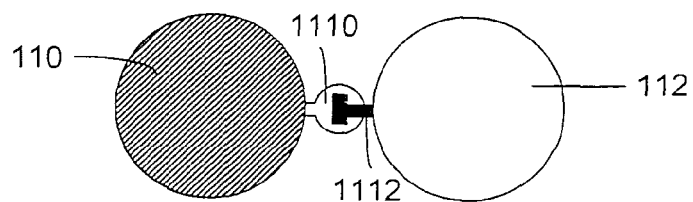

Some examples of the preceding embodiments are depicted in FIGS. 11A-11D. These are schematic depictions of exemplary configurations, and are not intended to be limiting. In FIG. 11A, a first bound composition comprises a luminescent material 110 and a first biotargeting agent 1101, and a second bound composition comprises a photosensitive biologically active material 112 and a second biotargeting agent 1102 (which may be the same as or different than the first biotargeting agent). FIG. 11B depicts an example in which the first and second bound compositions of FIG. 11A attach to a common substrate 1103 by way of the biotargeting agents 1101 and 1102, whereby the luminescent material and the photosensitive biologically active material are brought into proximity. The common substrate 1103 could be, for example, a tumor cell, a macromolecule (such as a protein), or some other feature for which the biotargeting agents 1101 and 1102 share an affinity. The biotargeting agents 1101 and 1102 are depicted as having a "y"-shape, which may suggest an exemplary embodiment in which the biotargeting agents are antibodies, and the common substrate 1103 is depicted as having a notched surface, which may suggest an exemplary embodiment in which the substrate is a cell that presents antigens on its surface, but these are symbolic depictions that are intended to encompass all manner of biotargeting agents and all manner of targets thereof. In FIG. 11C, a first bound composition comprises a luminescent material 110 and a first binding partner 1110 selected from a pair of binding partners, and a second bound composition comprises a photosensitive biologically active material 112 and a second binding partner 1112 selected from the pair of binding partners. In FIG. 11D, the first and second binding partners are bound together, whereby the luminescent material and the photosensitive biologically active material are brought into proximity. The binding partners 1110 and 1112 are depicted as having a complementary "lock" and "key" shapes, which may suggest an exemplary embodiment in which the binding partners are a protein and a corresponding protein ligand, but this is a symbolic depiction that is intended to encompass all manner of binding partners and binding action thereof.

FIG. 12 depicts in cross section an embodiment of the ionizing-radiation-responsive composition. The figure shows an illustrative configuration and is not intended to be limiting; other configurations will be apparent to those skilled in the art. In this configuration, the ionizing-radiation-responsive composition includes a core comprising a luminescent material 110, surrounded by an inner shell comprising a photosensitive biologically active material 112 and an outer shell comprising an adjuvant matrix or coating material 900. A biotargeting agent 1010 is attached to the outer shell. The embodiment further comprises a tagant material 1200. In the configuration depicted in FIG. 12, the tagant material is distributed as patches on the surface of the photosensitive biologically active material, but this is only an illustrative configuration and other configurations will be apparent to those skilled in the art. For example, the tagant material may be deposited on the outer surface of the bound composition, embedded in the interior of the bound composition, etc. In general, a tagant material is a material that facilitates detection, imaging, or dosimetry of the ionizing-radiation-responsive composition in situ, or that facilitates imaging, sensing, assay, or other measurement of the in situ environment. In a first embodiment, the tagant material may include a radioactive material, e.g. a gamma-active isotope of thallium, technetium, etc. that can be imaged with a SPECT camera or similar instrument. In a second embodiment, the tagant material may include a radiocontrast agent, e.g. a high-Z material (such as iodine, xenon, barium, or a lanthanide) that strongly absorbs or scatters imaging x-rays. In a third embodiment, the tagant material may include an MRI contrast agent, e.g. a gadolinium chelate or a magnetic nanoparticle. An MRI contrast agent can also function as a sensor, for example by conjugating the contrast agent to a sensing moiety such as a calcium-binding calmodulin protein (c.f. T. Atanasijevic et al, "Calcium-sensitive MRI contrast agents based on superparamagnetic iron oxide nanoparticles and calmodulin," PNAS 103 (2006), 14707-14712). In a fourth embodiment, the tagant material may include a fluorescent material, e.g. an organic dye, an inorganic dye, or a quantum dot. The fluorescent material can also function as a sensor or indicator dye; an example is the ruthenium-based dye $[Ru(dpp)_3]^{2+}$, which has an intensity decrease due to excited state quenching in the presence of molecular oxygen. Some examples of fluorescent dyes, sensor/indicator dyes, and quantum dot labels are described in T. Vo-Dinh et al, *Biomedical Photonics Handbook*, CRC Press, 2003, 56-1 to 56-20 and 58-1 to 58-14, herein incorporated by reference. E. Monson, supra, describes how various reference and indicator dyes can be incorporated into a nanoparticle matrix.

Figure 13:
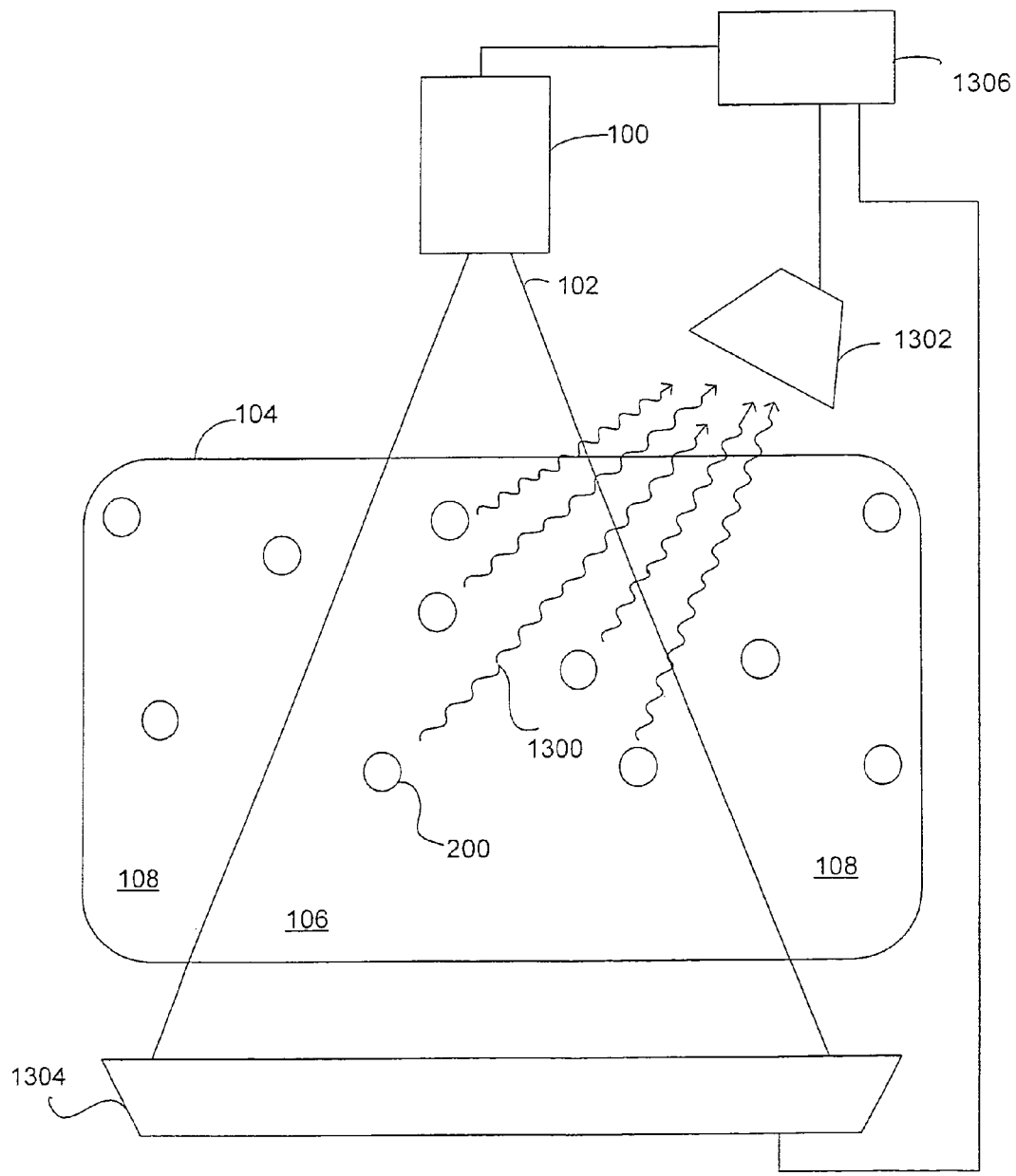
FIGS. 13-14 depict irradiation of an ionizing-radiation-responsive composition.

FIG. 13 depicts another illustrative embodiment and use in which an ionizing radiation emitter 100 produces ionizing radiation 102. The ionizing radiation irradiates at least a portion of a region 104 that contains an ionizing-radiation-responsive composition 200. As in FIG. 1 and FIG. 7, the luminescent material responds to ionizing radiation to produce optical energy, and the photosensitive biologically active material responds to optical energy to become biologically active (other embodiments provide other responses of the photosensitive biologically active material; for example, the photosensitive biologically active material may respond to the optical energy to become biologically inactive, to partially increase or decrease a level of biological activity, to change from a first mode of biological activity to second mode of biological activity, etc.). In the present embodiment, the ionizing-radiation-responsive composition additionally responds to ionizing radiation to produce scattered or luminescent radiation 1300. A first radiation detector 1302 is disposed to receive at least a portion of the scattered or luminescent radiation, and a second radiation detector 1304 is disposed to receive at least a portion of the ionizing radiation that is transmitted or forward scattered through the region 104. Other embodiments may include only the first radiation detector 1302 or only the second radiation detector 1304. The scattered or luminescent radiation 1300 might include, for example, Compton-scattered x-rays, pair production gamma rays, characteristic x-rays, or optical fluorescence. In those embodiments wherein the ionizing-radiation-responsive composition further comprises a tagant material, the scattered or luminescent radiation can originate from the tagant material. The first radiation detector 1302 can include, for example, one or more optical, x-ray, or gamma-ray sensors, optionally configured as a planar or tomographic imaging system (such as a CCD camera, optical tomograph, gamma camera, fluoroscope, PET scanner, SPECT scanner, or CT device). The second radiation detector 1304 can include, for example, one or more ionizing, radiation sensors (e.g. a semiconductor, phosphor, or scintillator detector), optionally configured as a planar or tomographic system (ibid).

The embodiment depicted in FIG. 13 further comprises a controller unit 1306 that is coupled to the ionizing radiation emitter, the first radiation detector, and the second radiation detector. The controller unit is configured to operate the ionizing radiation emitter, e.g. to activate or deactivate the emitter (or some portion thereof), change its mechanical position and orientation, and modulate the spectrum, intensity, beam shape, time sequence, etc. of the ionizing radiation. The controller unit is also configured to operate the first and/or second radiation detectors, e.g. to activate or deactivate either detector, change its mechanical position and orientation, vary the imaging or detection settings (such as the gain, spectral range, or field of view), and receive detection or imaging data. The controller unit can receive data from the first and/or second radiation detectors, determine a correlated photoactivated dosage of the photosensitive biologically active material, compare the correlated photoactivated dosage to a target photoactivated dosage, and adjust the operation of the ionizing radiation emitter to improve the correspondence between the correlated photoactivated dosage and the target photoactivated dosage. Additionally or alternatively, the controller unit can receive data from the first and/or second radiation detectors, which data comprises a map or image of the target region, and generate a radiation dosage profile corresponding to the map or image of the target region. For example, the ionizing-radiation-responsive composition may have a selective biological affinity for a particular tissue, tumor, or lesion, and thereby serve as an imaging contrast agent to reveal the spatial extent of the particular tissue, tumor, or lesion. Optionally the controller includes an interface module, which may include one or more user input devices (keyboards, pointing devices, microphones, etc.), one or more user output devices (video displays, speakers, etc.), one or more network interfaces (e.g. to access a computer network or database), or any combination thereof.

Figure 14:
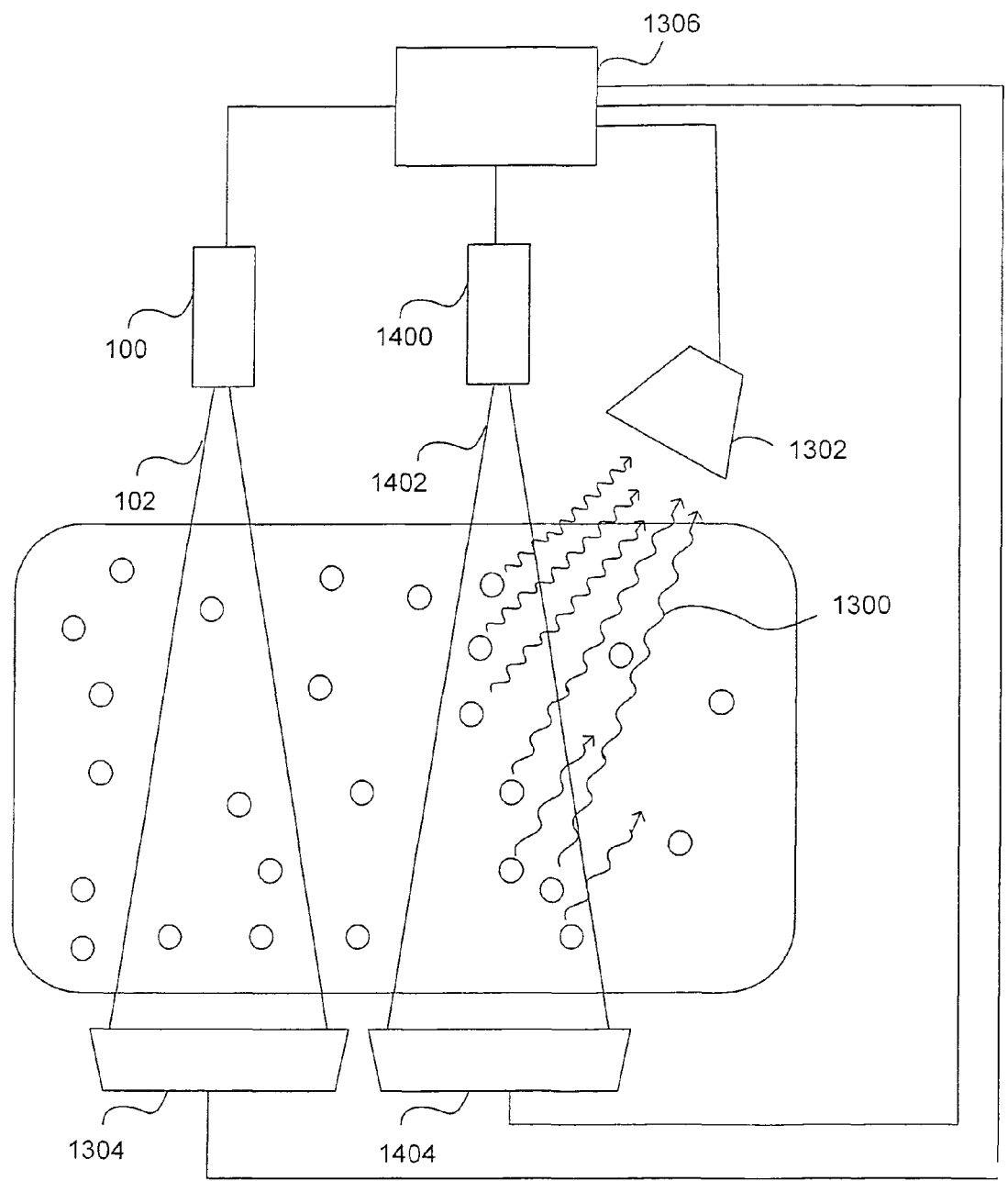

FIG. 14 depicts another illustrative embodiment and use in which an ionizing radiation emitter 100 produces ionizing radiation 102. The ionizing radiation irradiates at least a portion of a region 104 that contains an ionizing-radiation-responsive composition 200. The luminescent material responds to the ionizing radiation to produce optical energy, and the photosensitive biologically active material responds to optical energy to become biologically active (other embodiments provide other responses of the photosensitive biologically active material; for example, the photosensitive biologically active material may respond to the optical energy to become biologically inactive, to partially increase or decrease a level of biological activity, to change from a first mode of biological activity to second mode of biological activity, etc.). The present embodiment further comprises a probe radiation emitter 1400, which emits probe radiation 1402 that irradiates at least a portion of the region 104. The spatial extents of the ionizing radiation 102 and the probe radiation 1402 may be disjoint, as depicted in FIG. 14, or they may at least partially overlap. The ionizing-radiation-responsive composition responds to the probe radiation to produce scattered or luminescent radiation 1300. A first radiation detector 1302 is disposed to receive at least a portion of the scattered or luminescent radiation, a second radiation detector 1304 is disposed to receive at least a portion of the ionizing radiation that is transmitted or forward scattered through the region 104, and a third radiation detector 1404 is disposed to receive at least a portion of the probe radiation that is transmitted or forward scattered through the region 104. Other embodiments may include any one or any two of the three radiation detectors shown in FIG. 14. The probe radiation emitter 1400 might include, for example, an ionizing radiation emitter, an optical radiation emitter (especially one that operates at deeper-penetrating red or near-infrared wavelengths), or an RF antenna for nuclear magnetic resonance (when used in combination with an NMR magnet system, not shown). The scattered or luminescent radiation 1300 might include, for example, Compton-scattered x-rays, pair production gamma rays, characteristic x-rays, optical fluorescence, or NMR dipole radiation. In those embodiments wherein the ionizing-radiation-responsive composition further comprises a tagant material, the scattered or luminescent radiation can originate from the tagant material. The first radiation detector 1302 and the third radiation detector 1404 can include, for example, or one or more optical, x-ray, or gamma-ray sensors, optionally configured as a planar or tomographic imaging system (such as a CCD camera, optical tomograph, gamma camera, fluoroscope, PET scanner, SPECT scanner, or CT device). The first radiation detector can include one or more RF antennas, optionally configured as part of a magnetic resonance imaging system. The second radiation detector 1304 can include, for example, one or more ionizing radiation sensors (e.g. a semiconductor, phosphor, or scintillator detector), optionally configured as a planar or tomographic system (ibid).

The embodiment depicted in FIG. 14 further comprises a controller unit 1306 that is coupled to the ionizing radiation emitter, the probe radiation emitter, and the three radiation detectors. The controller unit is configured to operate the ionizing radiation and probe radiation emitters, e.g. to activate or deactive each emitter (or some portion thereof), change its mechanical position and orientation, and modulate the spectrum, intensity, beam shape, time sequence, etc. of the emitted radiation. The controller unit is also configured to operate the radiation detectors, e.g. to activate or deactivate a detector, change its mechanical position and orientation, vary the imaging or detection settings (such as the gain, spectral range, or field of view), and receive detection or imaging data. The controller unit can receive data from any or all of the radiation detectors, determine a correlated photoactivated dosage of the photosensitive biologically active material, compare the correlated photoactivated dosage to a target photoactivated dosage, and adjust the operation of the ionizing radiation emitter to improve the correspondence between the correlated photoactivated dosage and the target photoactivated dosage. Additionally or alternatively, the controller unit can receive data from any or all of the radiation detectors, which data comprises a map or image of the target region, and generate a radiation dosage profile corresponding to the map or image of the target region. For example, the ionizing-radiation-responsive composition may have a selective biological-affinity for a particular tissue, tumor, or lesion, and thereby serve as an imaging contrast agent to reveal the spatial extent of the particular tissue, tumor, or lesion. Optionally the controller includes an interface module, which may include one or more user input devices (keyboards, pointing devices, microphones, etc.), one or more user output devices (video displays, speakers, etc.), one or more network devices (e.g. to access a computer network or database), or similar devices and combinations thereof.

An illustrative embodiment is depicted as a process flow diagram in FIG. 15. This process flow may characterize, for example, the operation of the controller unit 1306 depicted in FIGS. 13 and 14. Flow 1500 includes step 1510—identifying a first process that at least partially converts ionizing radiation to an amount of optical energy. For example, ionizing radiation such as gamma rays or x-rays may be converted to optical energy by a luminescent material such as a scintillator or phosphor particle. Flow 1500 further includes step 1520—identifying a second process that at least partially converts the amount of optical energy to biological activity. For example, a photosensitive biologically active material may respond to optical energy to become biologically active, or a photosensitive bioactivity-adjusting material may respond to optical energy to allow release of a biologically active material. Flow 1500 further includes step 1530—responsive to the identifying a first process and the identifying a second process, determining an amount of ionizing radiation whereby a selected amount of biological activity is produced by a combination of the first process and the second process. For example, the first process may be characterized by an efficiency or cross section for conversion of ionizing radiation to optical energy (including spectral and in-situ dependencies thereof) and/or by a spatial distribution of a luminescent material that may accomplish the first process; the second process may be characterized by an efficiency or sensitivity for conversion of optical energy to biological activity (including spectral and in-situ dependencies thereof) and/or by a spatial distribution of a photosensitive biologically active material that may accomplish the second process; these characterizations of the first process and the second process can be used to determine an amount of ionizing radiation which should be delivered to obtain a selected amount of biological activity. The amount of ionizing radiation may include a specification of an irradiation energy spectrum, time profile, or spatial profile. Flow 1500 further includes step 1540—irradiating at least one region with the determined amount of ionizing, radiation. For example, an ionizing radiation emitter (e.g. a teletherapy device or CT instrument) may be operated to delivered the determined amount of ionizing radiation (optionally according to a specified time, space, and or energy profile). Flow 1500 optionally includes step 1550—detecting an amount of ionizing radiation that is transmitted or forward scattered through at least a portion of the at least one region. For example, an ionizing radiation detector (e.g. a semiconductor, phosphor, or scintillator detector, optionally configured as a planar or tomographic system) may be operated to detect the transmitted or forward-scattered ionizing radiation. Flow 1500 optionally further includes step 1555—determining an amount of biological activity corresponding to the detected amount of ionizing radiation. For example, there may be a correlation between the detected amount of transmitted or forward scattered ionizing radiation and the actual amount of biological activity caused by the irradiation in step 1540. Alternatively or additionally, the detected amount of transmitted or forward scattered ionizing radiation malt reveal characteristics of the in-situ environment (e.g. a spatial extent of a particular tissue, tumor, or lesion) whereon the amount of biological activity may depend (e.g. the biological activity is specific to a particular tissue, tumor, or lesion). Flow 1500 optionally further includes step 1580—adjusting the irradiating to obtain the selected amount of biological activity. For example, the ionizing radiation emitter may be adjusted (e.g. by activating or deactivating all or part of the emitter, changing its mechanical position or orientation, or modifying the spectrum, intensity, beam shape, time sequence, etc. of the ionizing radiation), whereby a discrepancy between the selected amount of biological activity (as used in step 1530 to determine an amount of ionizing radiation to administer) and the determined amount of biological activity (e.g. as obtained in step 1555, 1564, or 1576) may be at least partially removed or reduced.

Another illustrative embodiment is depicted as a process flow diagram in FIG. 16. This process flow may characterize, for example, the operation of the controller unit 1306 depicted in FIGS. 13 and 14. Flow 1600 includes steps 1510, 1520, 1530, and 1540, as described above. Flow 1600 optionally includes step 1560—identifying a third process that at least partially converts ionizing radiation to detectable radiation in at least one radiation mode, where the conversion by the third process at least partially corresponds to the conversion of ionizing radiation to biological activity by the combination of the first process and the second process. For example, an agent that accomplishes the first process and/or the second process (e.g. a luminescent material or a photosensitive biologically active material or a combination thereof), or a tagant material paired with such an agent, may respond to ionizing radiation to produce scattered or luminescent radiation (e.g. Compton-scattered x-rays, pair production gamma rays, characteristic x-rays, or optical fluorescence). Flow 1600 optionally further includes step 1562—detecting an amount of radiation in the at least one radiation mode. For example, a radiation detector (e.g. an optical, x-ray, or gamma-ray sensor, optionally configured as a planar or tomographic imaging system such as a CCD camera, gamma camera, fluoroscope, etc.) may be operated to detect radiation in the at least one radiation mode. Flow 1600 optionally further includes step 1564—determining an amount of biological activity corresponding to the detected amount of radiation in the at least one radiation mode. For example, there may be a correlation between the detected amount of radiation in the at least one radiation mode and the actual amount of biological activity caused by the irradiation in step 1540. Alternatively or additionally, the detected amount of radiation in the at least one radiation mode may reveal characteristics of the in-situ environment (e.g. a spatial extent of a particular tissue, tumor, or lesion) whereon the amount of biological activity may depend (e.g. the biological activity is specific to a particular tissue, tumor, or lesion). Flow 1500 optionally further includes step 1580, as described above.

Another illustrative embodiment is depicted as a process flow diagram in FIG. 17. This process flow may characterize, for example, the operation of the controller unit 1306 depicted in FIGS. 13 and 14. Flow 1700 includes steps 1510, 1520, 1530, and 1540, as described above. Flow 1700 optionally includes step 1570—identifying a third process that at least partially converts radiation in at least a first radiation mode to radiation in at least a second radiation mode, where the conversion by the third process at least partially corresponds to the conversion of ionizing radiation to biological activity by the combination of the first process and the second process. For example, an agent that accomplishes the first process and/or the second process (e.g. a luminescent material or a photosensitive biologically active material or a combination thereof), or a tagant material paired with such an agent, may respond to radiation in at least the first radiation mode (e.g. ionizing radiation, optical radiation, or RF radiation—the latter optionally originating from an RF antenna deployed as part of an NMR system) to produce scattered or luminescent radiation in at least the second radiation mode (e.g. Compton-scattered x-rays, pair production gamma rays, characteristic x-rays, optical fluorescence, or NMR dipole radiation). Flow 1700 optionally further includes step 1572—irradiating at least a portion of the at least one region with an amount of radiation in at least the first radiation mode. For example, a probe radiation emitter (e.g. ionizing radiation emitter, an optical radiation emitter, or an RF antenna used in combination with an NMR magnet system) may be operated to deliver the amount of radiation in at least the first radiation mode. Flow 1700 optionally further includes step 1574—detecting an amount of radiation in at least the second radiation mode. For example, a radiation detector (e.g. an optical, x-ray, or gamma-ray sensor, optionally configured as a planar or tomographic imaging system such as a CCD camera, gamma camera, fluoroscope, etc.; or one or more RF antennas, optionally configured as part of a magnetic resonance imaging system) may be operated to detect radiation in at least the second radiation mode. Flow 1700 optionally further includes step 1576—determining an amount of biological activity corresponding to the detected amount of radiation in at least the second radiation mode. For example, there may be a correlation between the detected amount of radiation in at least the second radiation mode and the actual amount of biological activity caused by the irradiation in step 1540. Alternatively or additionally, the detected amount of radiation in at least the second radiation mode may reveal characteristics of the in-situ environment (e.g. a spatial extent of a particular tissue, tumor, or lesion) whereon the amount of biological activity may depend (e.g. the biological activity is specific to a particular tissue, tumor, or lesion). Flow 1500 optionally further includes step 1580, as described above.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employs optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs ruining on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having still in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally) includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity, control motors for moving/distorting lenses to give desired focuses). A typical image processing system may be implemented utilizing any suitable commercially available components, such as those typically found in digital still systems and/or digital motion systems.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g. feedback for sensing position and/or velocity; control motors for moving and/or adjusting components and/or quantities). A typical data processing system may be implemented utilizing any suitable commercially available components, such as those typically found in data computing/communication and/or network computing/communication systems.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly, interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean al least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting with the true scope and spirit being indicated by the following claims.

What is claimed is:

1. A method, comprising:
   identifying a first process that at least partially converts ionizing radiation to an amount of optical energy;
   identifying a second process that at least partially converts the amount of optical energy to biological activity;
   responsive to the identifying a first process and the identifying a second process, determining an amount of ionizing radiation whereby a selected amount of biological activity is produced by a combination of the first process and the second process;
   irradiating at least one region with the determined amount of ionizing radiation;
   detecting an amount of ionizing radiation that is transmitted or forward scattered through at least a portion of the at least one region; and
   determining an amount of biological activity corresponding to the detected amount of ionizing radiation.

2. The method of claim 1, further comprising:

adjusting the irradiating to obtain the selected amount of biological activity.

3. A system, comprising:

means for identifying a first process that at least partially converts ionizing radiation to an amount of optical energy;

means for identifying a second process that at least partially converts the amount of optical energy to biological activity;

means, responsive to the means for identifying a first process and the means for identifying a second process, for determining an amount of ionizing radiation whereby a selected amount of biological activity is produced by a combination of the first process and the second process;

means for irradiating at least one region with the determined amount of ionizing radiation;

means for detecting an amount of ionizing radiation that is transmitted or forward scattered through at least a portion of the at least one region; and means for determining an amount of biological activity corresponding to the detected amount of ionizing radiation.

4. The system of claim 3, further comprising:

means for adjusting the irradiating to obtain the selected amount of biological activity.

5. A system, comprising:

circuitry for identifying a first process that at least partially converts ionizing radiation to an amount of optical energy;

circuitry for identifying a second process that at least partially converts the amount of optical energy to biological activity;

circuitry, responsive to the circuitry for identifying a first process and the circuitry for identifying a second process, for determining an amount of ionizing radiation whereby a selected amount of biological activity is produced by a combination of the first process and the second process;

circuitry for irradiating at least one region with the determined amount of ionizing radiation;

circuitry for detecting an amount of ionizing radiation that is transmitted or forward scattered through at least a portion of the at least one region; and circuitry for determining an amount of biological activity corresponding to the detected amount of ionizing radiation.

6. The system of claim 5, further comprising:

circuitry for adjusting the irradiating to obtain the selected amount of biological activity.

* * * * *